(12) United States Patent
Gunnewijk et al.

(10) Patent No.: US 7,371,581 B2
(45) Date of Patent: May 13, 2008

(54) PROCESS FOR THE MONITORING OF CONTAMINANT REMOVAL DURING THE PURIFICATION PROCESS OF A PHARMACEUTICAL PRODUCT PRODUCED BY A HOST CELL

(75) Inventors: Maria Gerarda Wilhelmina Gunnewijk, Groningen (NL); Jose Manuel Coco Martin, Roden (NL)

(73) Assignee: DSM IP Assets B.V., TE Heerlen (NL)

( * ) Notice: Subject to any disclaimer, the term of this patent is extended or adjusted under 35 U.S.C. 154(b) by 334 days.

(21) Appl. No.: 10/513,575

(22) PCT Filed: May 1, 2003

(86) PCT No.: PCT/NL03/00319

§ 371 (c)(1),
(2), (4) Date: Nov. 3, 2004

(87) PCT Pub. No.: WO03/093814

PCT Pub. Date: Nov. 13, 2003

(65) Prior Publication Data

US 2005/0170328 A1 Aug. 4, 2005

(30) Foreign Application Priority Data

Mar. 5, 2002 (EP) .................... 02076739

(51) Int. Cl.
*G01N 30/02* (2006.01)
*G01N 33/53* (2006.01)
*A23J 1/00* (2006.01)

(52) U.S. Cl. ...................... 436/161; 530/412; 530/416; 435/7.1; 435/7.92; 435/288.4; 435/288.7

(58) Field of Classification Search ............... None
See application file for complete search history.

(56) References Cited

U.S. PATENT DOCUMENTS

| 6,225,047 B1 | 5/2001 | Tai-Tung et al. |
| 6,579,719 B1 * | 6/2003 | Hutchens et al. ........... 436/161 |
| 2001/0053535 A1 | 12/2001 | Ladisch et al. |
| 2003/0207467 A1 * | 11/2003 | Snyder et al. .............. 436/518 |

OTHER PUBLICATIONS

Chu and Robinson, Curr. Opinion Biotechn. (2001) 12:180-187.
Costello Ma et al., Bioresponse (1988) 8:137 XP001087821.
International Search Report for PCT/NL03/00319, mailed on Sep. 3, 2003, 3 pages.
Jones et al., Biotechnol. Prog. (2003) 19:163-168.
Lin Shanhua et al., Proteomics (2001) 1(9):1172-1184.

* cited by examiner

*Primary Examiner*—Jon Weber
*Assistant Examiner*—Rita Mitra
(74) *Attorney, Agent, or Firm*—Nixon & Vanderhye, P.C.

(57) ABSTRACT

We describe a process for the monitoring of contaminant removal during the purification process of a pharmaceutical product produced by a host cell, wherein at least two different samples taken during the purification process of the pharmaceutical product are incubated with at least one protein biochip array and contaminants in the samples bound to the protein biochip array are subsequently detected. Preferably samples are taken before the first purification step and after each subsequent purification step.

15 Claims, 6 Drawing Sheets

Figure 1. NP20 (1) spectra. For clarity, not all the peaks are labelled.

Figure 2. ProteinChip NP20(2), 100 mM Na-Acetate (pH 4), 0.5 M NaCl
For clarity, not all peaks are labeled.

Figure 3. ProteinChip SAX2

For clarity, not all peaks are labeled.

Figure 4. Spectra of ProteinChip WCX2
For clarity, not all peaks are labeled.

Figure 5. ProteinChip WCX2 in more detail.
For clarity, not all peaks are labeled.

Figure 6. Spectra from ProteinChip H4
For clarity, not all peaks are labeled.

PROCESS FOR THE MONITORING OF CONTAMINANT REMOVAL DURING THE PURIFICATION PROCESS OF A PHARMACEUTICAL PRODUCT PRODUCED BY A HOST CELL

CROSS-REFERENCE TO RELATED APPLICATIONS

This application is the national phase of PCT application PCT/NL03/00319 having an international filing date of 1 May 2003, which claims priority from European application 02076739.8 filed 3 May 2002. The contents of these documents are expressly incorporated herein by reference for all purposes.

BACKGROUND OF THE INVENTION

The invention relates to a process for the monitoring of contaminant removal during the purification process of a pharmaceutical product produced by a host cell.

Monitoring the removal of contaminants during the purification process of a pharmaceutical product produced by a host cell is necessary to acquire market approval of the pharmaceutical product. For market approval of the pharmaceutical product, it must be shown that the purification process is reproducible and that the pharmaceutical product is produced with a constant quality (i.e. purity). Therefore, there is a need for reliable methods for monitoring contaminant removal during the purification process of a pharmaceutical product.

Detection methods used for the monitoring of contaminant removal during the purification process of a pharmaceutical product produced by a host cell are known in the art. The known methods make use of immunological methods, for example ELISA or Western blot mostly combined with other known methods not based on immunology, for example 1- and 2D-gelelectrophoresis or (reversed phase) HPLC.

A disadvantage of the known immunological methods is that the used antibodies are raised against certain proteins only. Typically, antibodies are only raised against immunogenic host cell proteins. Therefore, contaminants other than said immunogenic host cell proteins cannot be detected by immunological methods.

In immunological methods, polyclonal antibodies raised against (host cell) proteins in a host animal (e.g. rabbit, goat, mouse) are usually used. Therefore, immunological methods can only detect the (host cell) proteins that are capable of inducing an immunological response in the host animal. Typically, this accounts for the detection of only 20-30% of the total (host cell) proteins. As polyclonal antibodies are usually not raised in humans, the remaining non-detected host cell proteins may well cause an immunological reaction in humans. In addition, other contaminants besides (host cell) proteins are not detected either.

The disadvantage of both the immunological and the other known detection methods not based on immunological detection is that they do not have a high sensitivity combined with the ability to detect individual proteins; the known methods either detect individual proteins with a relatively low sensitivity (Western blot, HPLC, 1- and 2-D gelelectrophoresis) or detect a total protein signal with a higher sensitivity (e.g. ELISA).

SUMMARY OF THE INVENTION

It is the object of the invention to provide a process for the monitoring of contaminant removal during the purification of a pharmaceutical product produced by a host cell, which method has the ability to detect individual proteins with a relatively high sensitivity.

This object is achieved by the invention by incubating at least two different samples taken during the purification process of the pharmaceutical product with at least one protein biochip array and by subsequent detection of the contaminants bound to the protein biochip array.

DETAILED DESCRIPTION OF THE INVENTION

Protein biochip arrays are known in the art and are commercially available from for example Biacore (Upsala, Sweden) and Ciphergen Biosystems (Fremont, Calif., USA). Uptil now, protein biochip arrays have been used for isolation of a product and for the analysis of cell components (e.g. for differential gene expression studies) (U.S. Pat. No. 6,225,047).

It has surprisingly been found that protein biochip arrays are extremely capable of monitoring the contaminant removal during the purification process of a pharmaceutical product produced by a host cell and that the detection of individual proteins occurs with a relatively high sensitivity. Moreover protein biochip arrays are capable of binding both proteins and other contaminants, whereas the known immunological methods can only detect proteins and whereas the other known methods not based on immunology can detect either proteins only or contaminants only.

The term 'pharmaceutical product' means, proteins (e.g. antibodies, receptors, enzymes, fusion proteins etc.), which can be used as an active ingredient in pharmaceutical preparations, (plasmid) DNAs with a medical application, for example, for use in gene therapy, or vaccines.

The term 'contaminant' means all compounds present in the pharmaceutical product other than the desired pharmaceutical product itself. Contaminants are for example, (host cell) proteins, contaminants from the cell culture medium wherein the pharmaceutical product is produced by the host cell, additives added during the purification process, for example column leechables, stabilizing agents, virus inactivating agents, small organic molecules etc.

Purification processes for a pharmaceutical product produced by a host cell generally comprise several purification steps in varying combinations and order. Examples of purification steps are separation steps (e.g. by affinity chromatography and/or ion exchange chromatography), whereas other steps are for example needed to concentrate the pharmaceutical product (e.g. by ultrafiltration or diafiltration), steps to exchange buffers or steps to remove or inactivate viruses (e.g. by virusfiltration, pH shift or solvent detergent treatment).

Monitoring the purification of a pharmaceutical product according to the invention is done by incubating at least two different samples taken during the purification process of the pharmaceutical product with at least one protein biochip array and subsequent detection of the contaminants bound to the protein biochip array. Comparison of the obtained detection results shows the effect of the purification. When the samples are taken is not really critical as long as the effect of the purification can be seen from the comparison of the detection results of the different samples. In practice, preferably, samples are taken between two purification steps. More preferably, samples are taken at least before the first purification step and after the last purification step. Most preferably, samples are taken before the first purification step and after each subsequent purification step.

Protein biochip arrays have an interactive surface to which proteins can bind. The interactive surface may be for example of a chemical nature, for example a ligand of a certain receptor or a chromatographic surface or a biological surface. Chromatographic surfaces include, but are not limited to aliphatic hydrophobic surfaces; aromatic hydrophobic surfaces; negatively-charged, cation exchange surfaces; positively-charged, anion exchange surfaces; immobilized metal affinity chromatographic surfaces; and mixed mode surfaces, comprising for example a negatively-charged, cation exchange surface and a positively-charged, anion exchange surface. Chromatographic surfaces are for example also described in U.S. Pat. No. 6,225,047. Biological surfaces include, but are not limited to covalently linked antibodies, DNA, enzymes, receptors, ligands and single chain variable antibodies or antibody like ligands (the latter two of which can be obtained from a phage display library).

The nature of the interactive surface determines which contaminants are bound. If, for example, the protein biochip array has an interactive surface comprising single chain variable antibodies or antibody like ligands obtained from a phage display library against host cell proteins, most of the host cell proteins will be detected (and not only those host cell proteins capable of inducing an immunological response in a host animal).

In a preferred embodiment of the invention, a sample obtained after a given purification step is incubated with at least two, more preferably at least three, most preferably at least four different protein biochip arrays with different interactive surfaces in the process according to the invention. The use of more different protein biochip arrays alongside each other has the advantage that more different contaminants can be detected.

Contaminants bound to the protein biochip array surface can be detected directly. Examples of techniques suitable for direct detection include photometric approaches monitoring refractive index change, for instance approaches using surface plasmon resonance (SPR), fluorescence or polarization change; and mass spectrometric approaches, for instance SELDI (surface enhanced laser desorption ionization).

Alternatively, contaminants may also be detected indirectly; in this case contaminants bound to the protein biochip array are eluted from the array and carried to a detector in a stream of eluent. Examples of techniques suitable for indirect detection include electrospray ionisation (ESI) or matrix-assisted laser desorption/ionization (MALDI). Preferably in the process according to the invention, the contaminants are detected directly, preferably using a mass spectrometric approach.

Preferably, in the process according to the invention, a direct detection method, more preferably mass spectrometry is used for the detection of the contaminants bound to the protein biochip array in the process according to the invention.

The process according to the invention is preferably used for the monitoring of protein removal, more preferably host cell protein removal from the pharmaceutical product.

Host cells, which can be used to produce pharmaceutical products are in principle all cells known to the person skilled in the art, which have the ability to produce a pharmaceutical protein, (plasmid) DNA or vaccine. Examples of host cells are eukaryotic cells, for instance philamentus fungi, for example *Aspergillu niger, Aspergillus oryzae, Trichoderma reesei, Penicillium chrysogenum*, yeasts, for example *Saccharomyces cerevisiae, Phaffia rhodozyma, Pichia pastoris*, mammalian cells, for example CHO (Chinese Hamster Ovary) cells, hybridomas, BHK (Baby Hamster Kidney) cells, myeloma cells, human cells, for example HEK-293 cells, human lymphoblastoid cells and prokaryotic cells, for instance *Escherichia coli, Bacillus* sp, for example *B. licheniformis, B. subtilis, B. amyloliquefaciens, B. alkalophilus, Streptomyces* sp., *Corynebacterium glutamicum, Pseudomonas* sp. Examples of eukaryotic cells are for example also described in Chu, L., Robinson, D. K., (2001) Curr. Opinion Biotechn., vol. 12, p. 180-187.

Examples of proteins that can be used as an active ingredient in pharmaceutical preparations (with the brand name of the corresponding pharmaceutical between brackets) are for example Tenecteplase (TN Kase™), (recombinant) antihemophilic factor (ReFacto™), lymphoblastoid Interferon α-n1 (Wellferon™), (recombinant) Coagulation factor (NovoSeven™), Etanercept, (Enbrel™), Trastuzumab (Herceptin™), Infliximab (Remicade™), Palivizumab (Synagis™), Basiliximab (Simulect™), Daclizumab (Zenapaz™), Rituximab (Rituxan™), (recombinant) Coagulation factor IX (Benefix™) and Interferon β-1 a (Avonex™).

Examples of DNAs with a possible medical application are gene therapeutic plasmid DNAs. Some gene therapeutic plasmid DNAs are presently tested in clinical trials for their medical application.

Examples of vaccines are live, oral, tetravalent Rotavirus vaccine (RotaShield™), rabies vaccine (RanAvert™) and inactivated hepatitis A vaccine (VAQTA™).

The invention also relates to the use of one or more protein biochip arrays for the monitoring of contaminant removal during the purification process of a pharmaceutical product produced by a host cell. Preferably to the use of at least two, more preferably at least three, most preferably at least four different protein biochip arrays with different interactive surfaces. Preferably, the contaminants are proteins, more preferably host cell proteins.

The invention will now be elucidated by way of the following example without, however, being limited thereto.

EXAMPLES 1.0 Introduction

In this study we followed the removal of contaminants during the partial purification of a human recombinant IgG1 (2) by SELDI-TOF-MS (Ciphergen). The IgG1 is expressed in the PER.C6 cell line which was generated from retinaderived primary human cells. The PER.C6 cell line is able to generate completely human monoclonal antibodies (including the glycans) (1, 2).

The contaminants present in the samples collected during the purification process were analyzed by using Protein-Chips. The ProteinChips (Ciphergen) have an interactive surface to which proteins can bind. We used the normal phase ProteinChip (NP20), the strong anion exchange ProteinChip (SAX2), the weak cation exchange ProteinChip (WCX2) and the hydrophobic interaction PorteinChip (H4) under different binding conditions.

2.0 Materials and Methods

2.1 Fermentation and Purification.

The PER.C6 cells expressing human IgG1 (2) were grown in 2 L EX-CELL VPRO medium (JRH Biosciences, Inc., USA) in a batch culture for 13 days at 37° C. with an agitation speed of 75 rpm using two empellers. The cells and supernatant were separated by centrifugation for 5 min at 300 g at room temperature (R.T.), the supernatant was subsequently filtered over a 22 μm filter (Millipak 20, Millipore). Of this clarified material a sample was taken for analysis by SELDI-TOF-MS (Sample 1, Table 1). A volume of 100 ml clarified and filtrated harvest was applied on a recombinant protein A column (13.8 cm bed height and a volume of 13.1 mL, Pharmacia Biotech) which was connected to an Akta Explorer chromatography system (Pharmacia Biotech). Before the application of the clarified harvest the column was equilibrated with 3 column volumes of 20 mM Tris (pH 7.5), 150 mM NaCl at 1.67 mL/min. While the clarified harvest was applied at 1.67 mL/min a sample was taken from the flow through (Sample 2, Table 1). After washing the column with 10 column volumes 20 mM Tris (pH 7.5), 150 mM NaCl at 1.67 mL/min the column was brought to 0.1 M citrate pH 5.0 in 10 column volumes at 1.67 mL/min). The IgG1 was eluted from the column by 5 column volumes 0.1 M citrate pH 3.3 and was subsequently neutralized with 1 M Tris-HCl (pH 9) (Sample 3, Table 1). The elution of proteins was followed by measuring the absorption at 280 nm.

TABLE 1

Collected intermediates for analysis by
SELDI-TOF-MS during purification of IgG1.

| Sample | Indication | [Product] (g/l)* | Buffer |
| --- | --- | --- | --- |
| 1 | Medium | 0 | n.a. |
| 2 | Clarified harvest | 0.5 | n.a. |
| 3 | Flow Through | 0 | 20 mM Tris-HCl, 150 mM NaCl (pH 7.5) |
| 4 | Eluate | 1 | 0.08 M Na-citrate, 0.2 M Tris-HCl (pH 8) |

*Determined from absorption at 280 nm ($\epsilon = 1.171\ M^{-1} \cdot cm^{-1}$)
n.a., not applicable

2.2 Intermediates on an NP20 ProteinChip.

In this experiment two different energy absorbing matrices (EAMs) were used, saturated sinapinic acid (SPA) and a 20% saturated solution of alpha-cyano4-hydroxy cinnaminic acid (CHCA) both in 50% acetonitrile (ACN), 0.5% trifluoracetic acid (TFA). The samples were analyzed as described in the experimental procedure below (2.2.1). To obtain a product concentration of 0.15 g/L, sample 2 and sample 4 were diluted 3.3 and 6.6 times, respectively, with phosphate buffered saline (PBS), pH 7.4. Then, of each sample (sample 2 and 4 diluted and 1 and 3 undiluted) 3 μl was added to a spot. Sample 1, 2, 3 and 4 were applied on spot A, B, C and D and again on E, F, G and H. Spots A to D were analyzed with CHCA and E to H with SPA.

2.2.1 Experimental Procedure

Calibrate the SELDI-TOF-MS for the low molecular weight analysis using molecular weight standard C100-0003 (Ciphergen) according to the protocol supplied by the manufacturer.

Calibrate the SELDI-TOF-MS for the high molecular weight analysis using molecular weight standard C100-0004 (Ciphergen) according to the protocol supplied by the manufacturer.

Take one cup with EAM (both SPA and CHCA, 5 mg, Ciphergen), add 125 μL ACN and 125 μL 1% TFA (freshly prepared by adding 5 μL TFA to 495 μL HPLC grade water). Vortex for 5 min and allow to stand at room temperature for 5 min.

Microfuge for 5 min at maximum speed

Use the supernatant of the SPA as the saturated SPA solution.

Make the 20% CHCA solution by taking 100 μL saturated CHCA solution and add to 200 μL ACN, 200 μL 1% TFA Store EAM-solutions until use in the dark at 4° C.

Pre-wet each spot with 3 μL HPLC grade water.

Remove the HPLC grade water and immediately apply 3 μL of one sample per spot.

Allow the spots to air dry

Wash each spot with 5 μL HPLC grade water

Allow to dry and repeat the wash once

Apply 0.8 μL SPA/CHCA

Allow the chip to air dry (5 min in hood)

Apply another 0.8 μL SPA/CHCA and dry

Analyze the chip with the instrument settings given below

2.2.2 Instrument Settings

For Low Molecular Weight 0-10 kDa (SPA as EAM)
Set high mass to 10000 Daltons, optimized from 1000 Daltons to 7500 Daltons.
Set starting laser intensity (LI) to 180.
Set starting detector sensitivity to 6.
Focus lag time at 600 ns.
Set data acquistion method to Seldi Quantitation
Set Seldi acquisition parameters 21. delta to 2. transients per to 5 ending position to 81.
Set warming positions with 2 shots at intensity 185 and Don't include warming shots.
Process sample.

For High Molecular Weight 10200 kDa (SPA as EAM)
Set high mass to 200000 Daltons, optimized from 10000 Daltons to 150000 Daltons.
Set starting Li to 230.
Set starting detector sensitivity to 9.
Focus by optimization center.
Set data acquistion method to Seldi Quantitation
Set Seldi acquisition parameters 20. delta to 4. transients per to 10 ending position to 80.
Set warming positions with 2 shots at intensity 240 and Don't include warming shots.
Process sample.

For Low Molecular Weights (CHCA as EAM)
Set high mass to 15000 Daltons, optimized from 1000 Daltons to 10000 Daltons.
Set starting Li to 180.
Set starting detector sensitivity to 9.

Focus by optimization center.
Set data acquistion method to Seldi Quantitation
Set Seldi acquisition parameters 21. delta to 5. transients per to 10 ending position to 79.
Set warming positions with 2 shots at intensity 185 and Don't include warming shots.
Process sample.

Spectra were analyzed using the peak detection software supplied by the manufacturer (Ciphergen, Fremont, Calif., USA) in the software package Ciphergen ProteinChip Software 3.0.1. Peaks with a signal/noise ratio (S./N) of 2 or more were included in the comparison studies. The area for shoulder peaks is given as zero.

2.3 The Detection on SAX2, WCX2, NP20 and H4 ProteinChips under Varying Conditions Using SPA as the EAM.

Samples 1-4 were applied on a SAX2, WCX2, NP20 and H4 ProteinChip. Sample 1 and 4 were used in the same dilution as indicated for the first NP20. The samples were analyzed according the experimental procedure described in 2.3.1 with the instrument settings of 2.3.2.

TABLE 2

The first equilibration and two different buffers.

| Array | Equilibration buffer | Spot A-D Binding/wash buffer 1 | Spot E-H Binding/wash buffer 2 |
|---|---|---|---|
| H4 | 50% Acetonitrile | PBS (pH 7.4), 1 M NaCl, 10% ACN | PBS (pH 7.4), 1 M NaCl, 30% ACN |
| NP20 | Water | 0.5 M NaCl, 100 mM Na-acetate, pH 4 | PBS, pH 7.4, 0.5 M NaCl |
| WCX2 | n.a | 100 mM Sodium Acetate (pH 4) + 0.1% Triton X-100 | 100 mM Sodium Acetate (pH 6) + 0.1% Triton X-100 |
| SAX2 | n.a. | 100 mM Tris (pH 9) + 0.1% Triton X-100 | 100 mM Sodium Acetate (pH 6) + 0.1% Triton X-100 | n.a., not applicable 2.3.1 Experimental Procedure
Assemble the bioprocessor with the different chips
Equilibrate the H4 and NP20 chip by adding 50 μL equilibration buffer (Table 2) to each spot and shake for 5 min at 300 rpm.
Then equilibrate the spots of all ProteinChips by adding 50 μL of the appropriate binding buffer as indicated in Table 2.
Dispense 90 μL of binding buffer into the wells
Add 10 μL of aliquot sample in the solution
Take extreme care not to form bubbles at the bottom of the wells
Mix by pipetting up and down four times
Add all the samples in this way
Cover the bioprocessor with seal foil
Shake the array assembly for 60 min on a vortex shaker (R.T., 350 rounds/s)
Flick the solutions in the sink and slab the bioprocessor on a cleanroom wipe.
Wash arrays 3 times with 150 μl the binding buffer by shaking for 5 min at R.T.
Quickly wash each array with 150 μl de-ionized (DI) water for 1 min.
Remove the chip(s) from the Bioprocessor
Dry excess liquid outside the spot with a paper tissue
Allow to dry to the air
Apply 0.8 μl saturated SPA solution (see 2.2.1 for preparation)
Allow to dry
Apply second 0.8 μl of the saturated SPA solution
Allow to dry
Read chip
Store chips in the dark at R.T. until analysis.

2.3.2 Instrument Settings
Set high mass to 200000 Daltons, optimized from 10000 Daltons to 150000 Daltons.
Set starting Li to 230 or 270, respectively
Set starting detector sensitivity to 9.
Focus by optimization center.
Set data acquistion method to Seldi Quantitation
Set Seldi acquisition parameters 20 or 21, respectively
Delta to 5 transients per to 10 ending position to 80 or 81, respectively.
Set warming positions with 2 shots at intensity 235 or 275, respectively
Don't include warming shots.
Process sample.

3.0 Results

No additional peaks were found in the low molecular range using either CHCA or SPA as the EAM on the ProteinChip NP20. Therefore, the other ProteinChips were analyzed with SPA as the EAM, allowing detection of impurities in both the high and low molecular range.

From the difference between the spectra of the medium and the clarified harvest, produced proteins/impurities by the host cell (including product) were identified. In the spectrum of the flow through, many of these impurity peaks are encountered indicating that the impurities were separated from the product (see the added figures and/or tables). The product is present around 148 kDa in its single charged form (IgG1+H), it is also present at 74 kDa in its doubly charged form (IgG1+2H) and sometimes even in its triply charged form around 49 kDa (IgG1+3H), these peaks are indicated in bold.

For the first NP20 ProteinChip (NP20(1)) the data obtained with SPA (spot E-H) analyzed with LI 230 are given. For the other chromatographic surfaces the data obtained with either LI 230 or LI 270 are given. The percentage of impurities can only be calculated when a product peak is present, thus only for the clarified harvest (sample 2) and the eluate (sample 3). For the calculation the following formula (1) was used.

TABLE 3

% Impurities calculated for clarified harvest (sample 2) and the eluate (sample 3) found for the different ProteinChips.

| Sample | | ProteinChip | | | | |
|---|---|---|---|---|---|---|
| | | NP20 (1)° | NP20 (2)* | SAX2° | WCX2* | H4* |
| Sample 2 | Clarified harvest | 87 | 94/92 | 94/97 | 97/90 | n.a./89 |
| Sample 3 | Eluate | 15 | 14/17 | 21/33 | 25/14 | 17/19 |
| | Removal | 72 | 80/75 | 73/64 | 72/76 | —/75 |

When applicable, before the forward slash the results from spots A-D and after the forward slash those from spots E-H are given.
*obtained with LI 270;
°obtained with LI 230;
n.a., not applicable since no IgG was detected.

By comparing the spectra of the medium before and after the fermentation contaminants produced by the host cell can be identified and subsequently followed during the purification. By comparing the masses of each spectrum unique peaks per intermediate per proteinchip can be identified, which may give additional insight in the amount or removal of impurities. Impurities with masses within 0.5% difference are considered identical.

4.0 Conclusions

Figure 1:
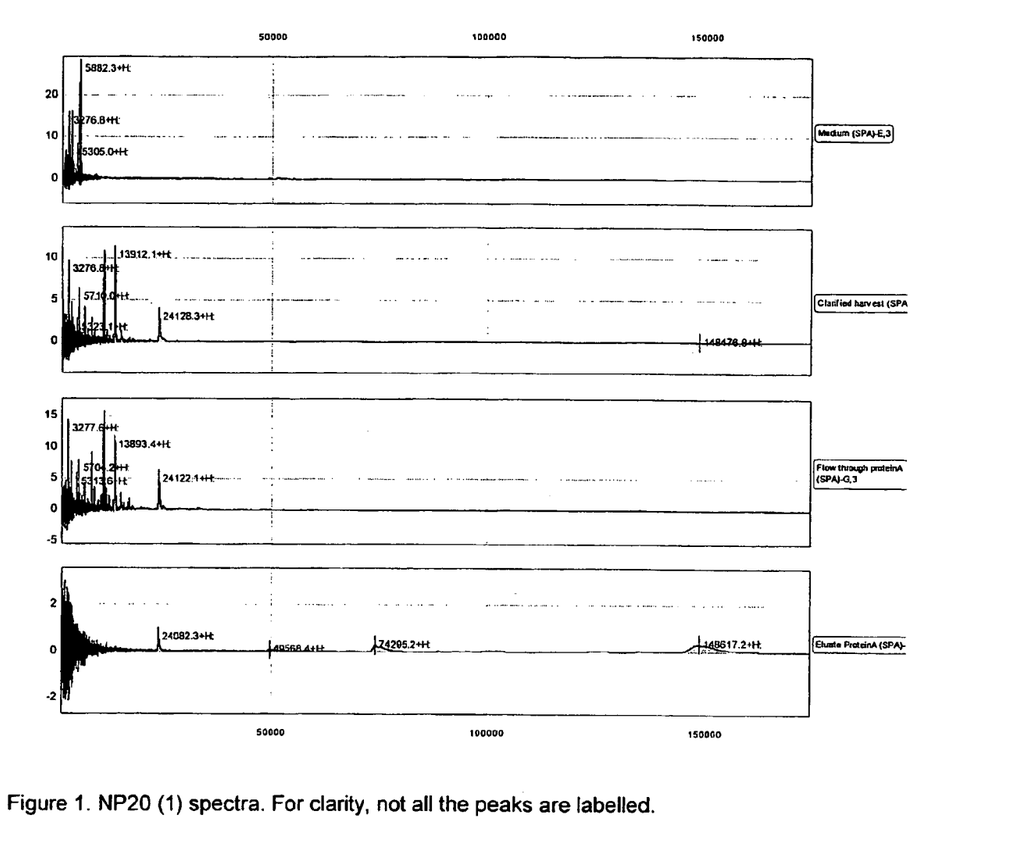
FIG. 1 shows spectra of ProteinChip NP20(1). For clarity, not all the peaks are labeled.
Figure 2:
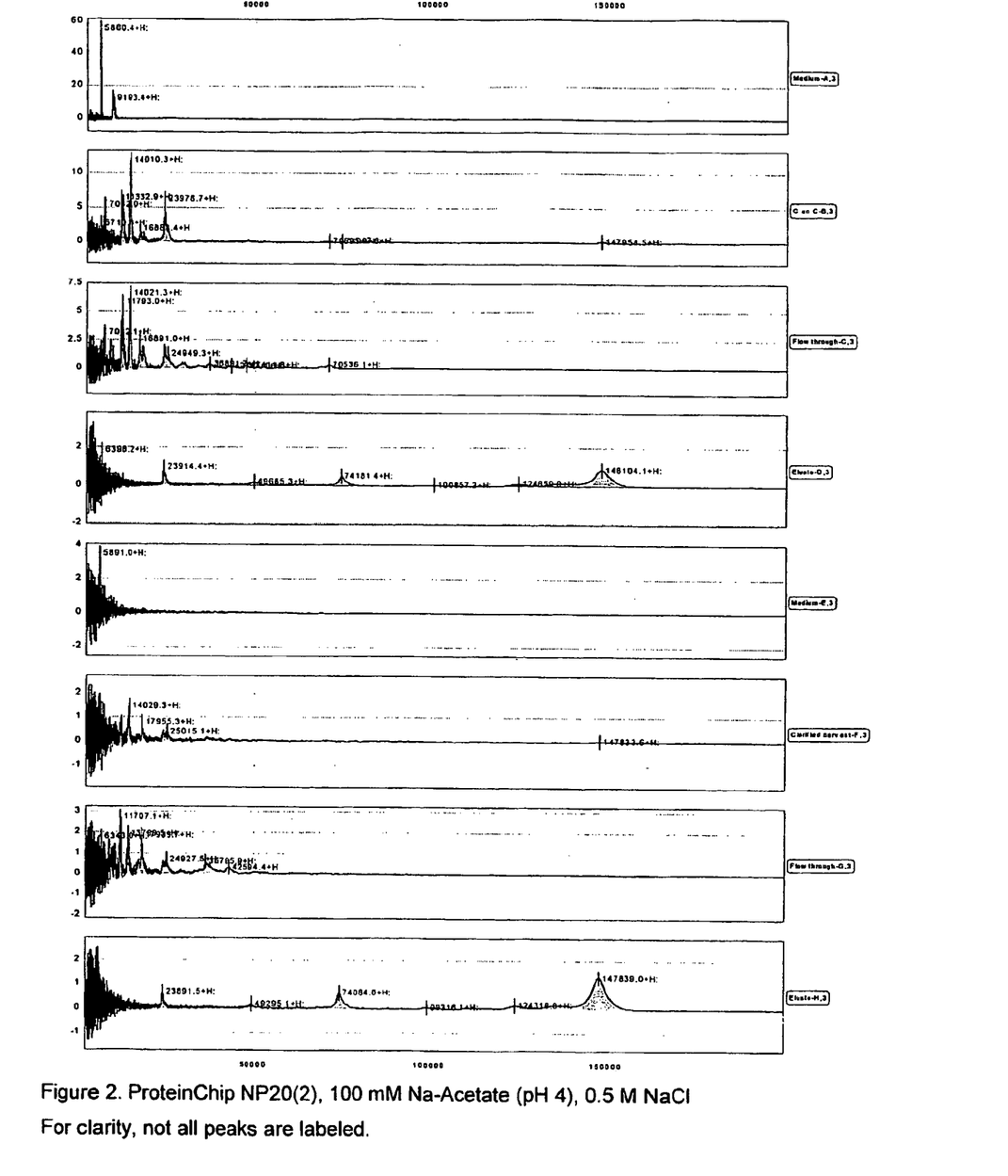
FIG. 2 shows spectra of ProteinChip NP20(2). For clarity, not all peaks are labeled.
Figure 3:
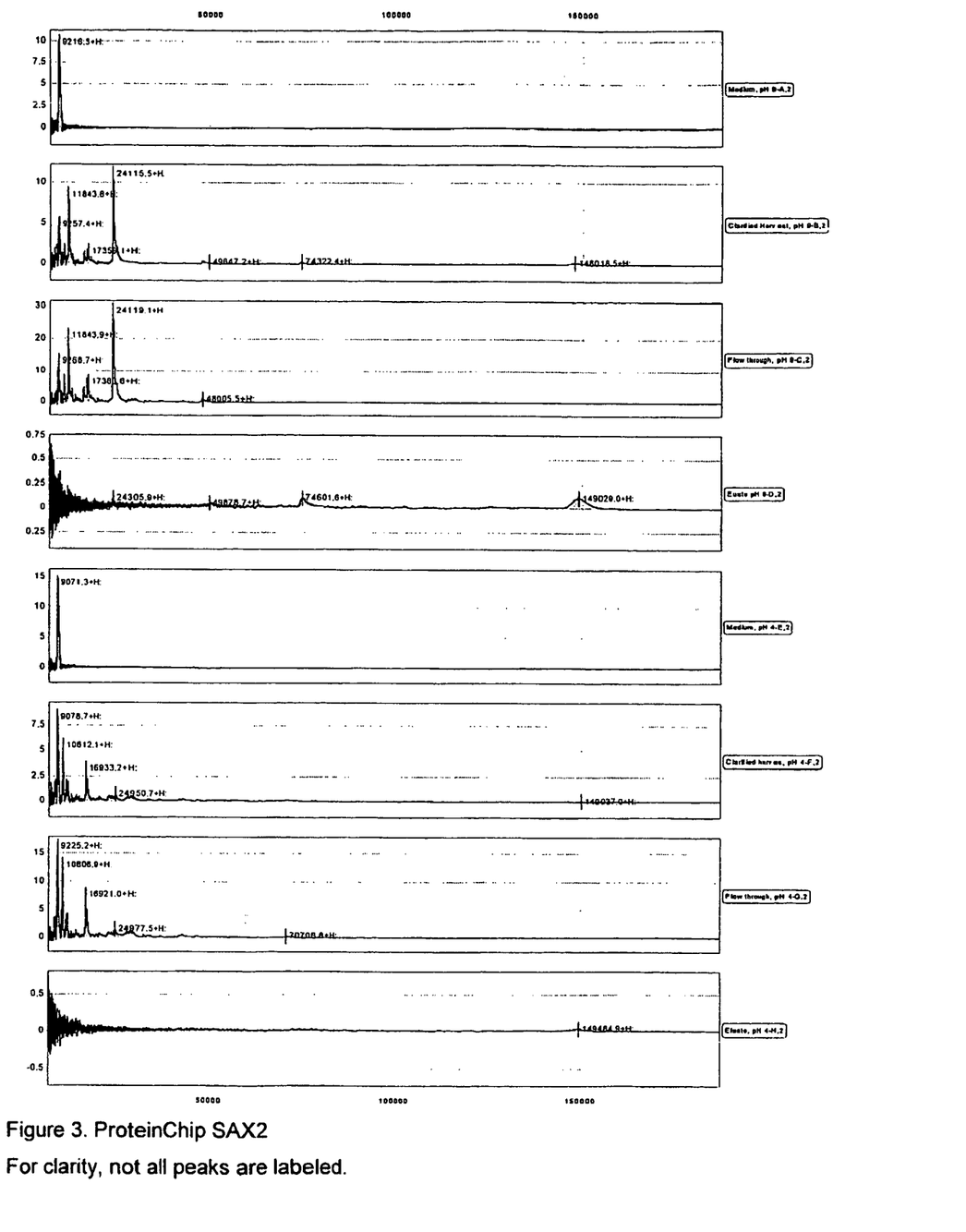
FIG. 3 shows spectra of ProteinChip SAX2. For clarity, not all peaks are labeled.
Figure 4:
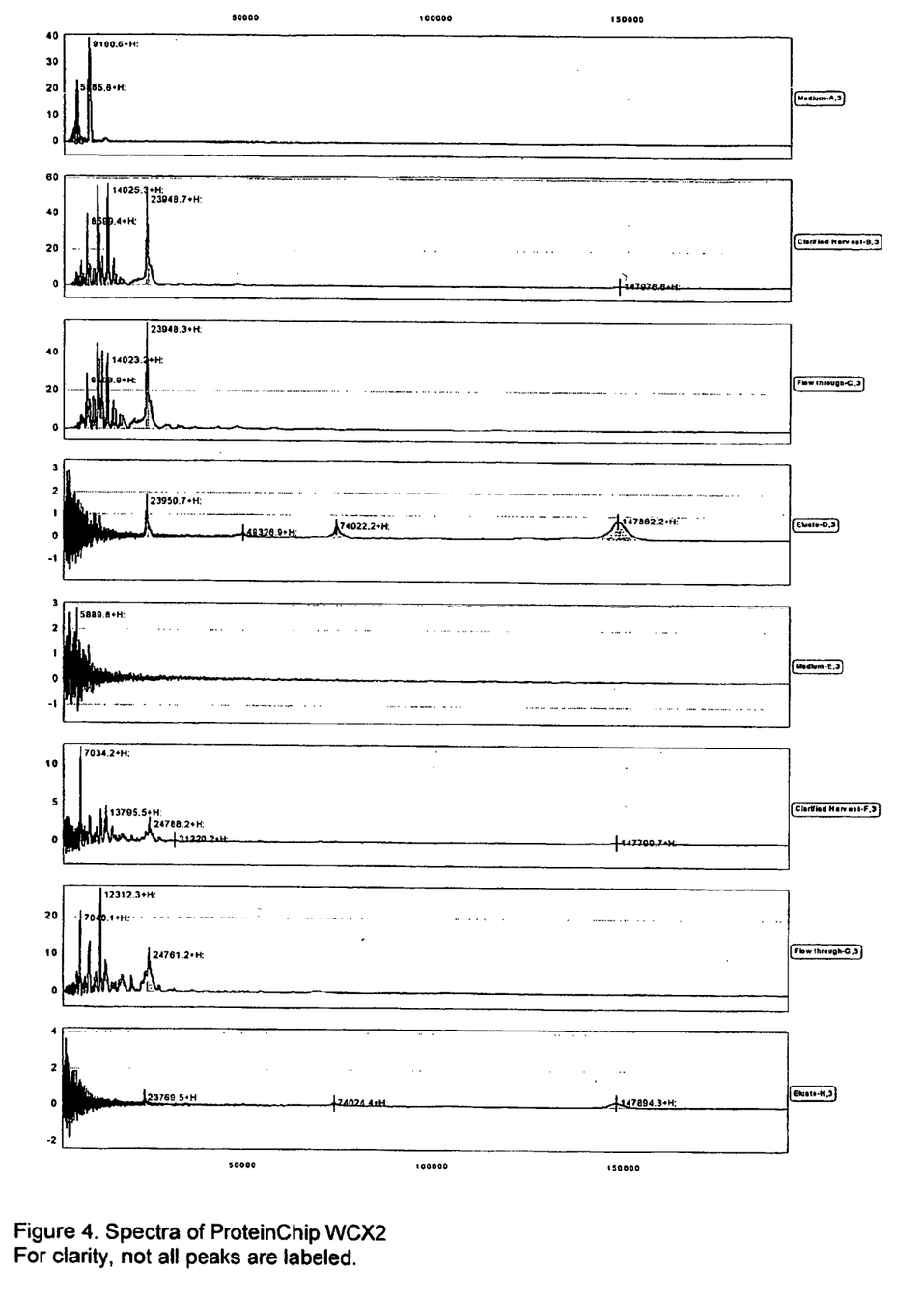
FIG. 4 shows spectra of ProteinChip WCX2. For clarity, not all peaks are labeled.
Figure 5:
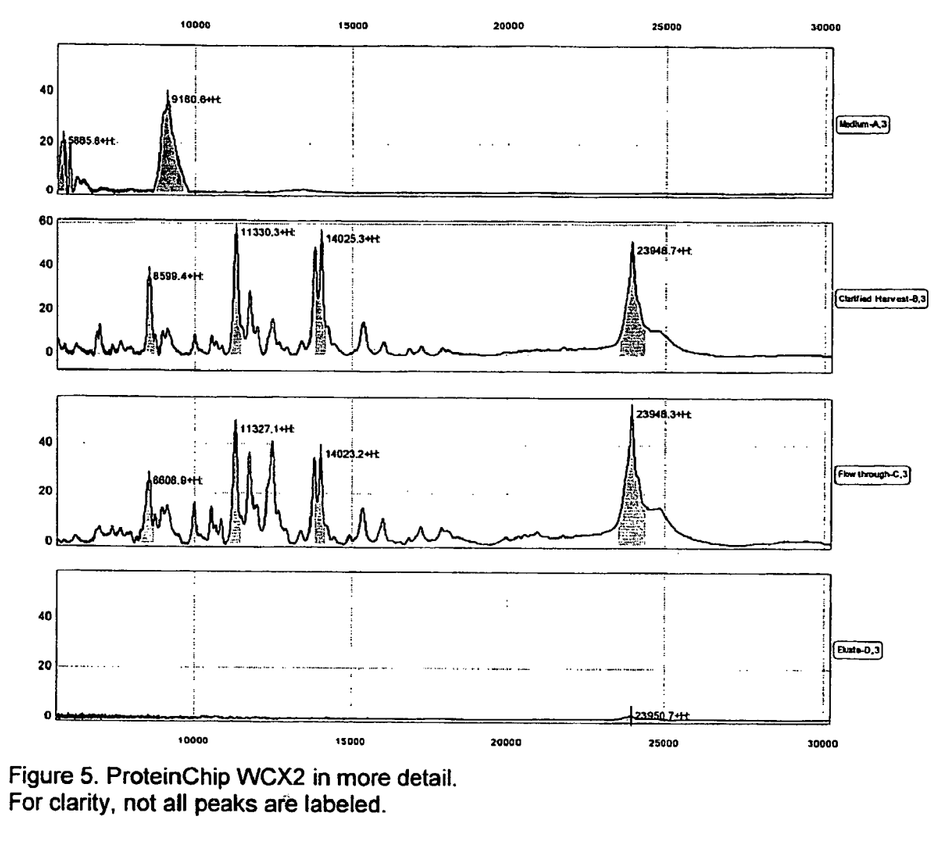
FIG. 5 shows spectra of ProteinChip WCX2 in more detail. For clarity, not all peaks are labeled.
Figure 6:
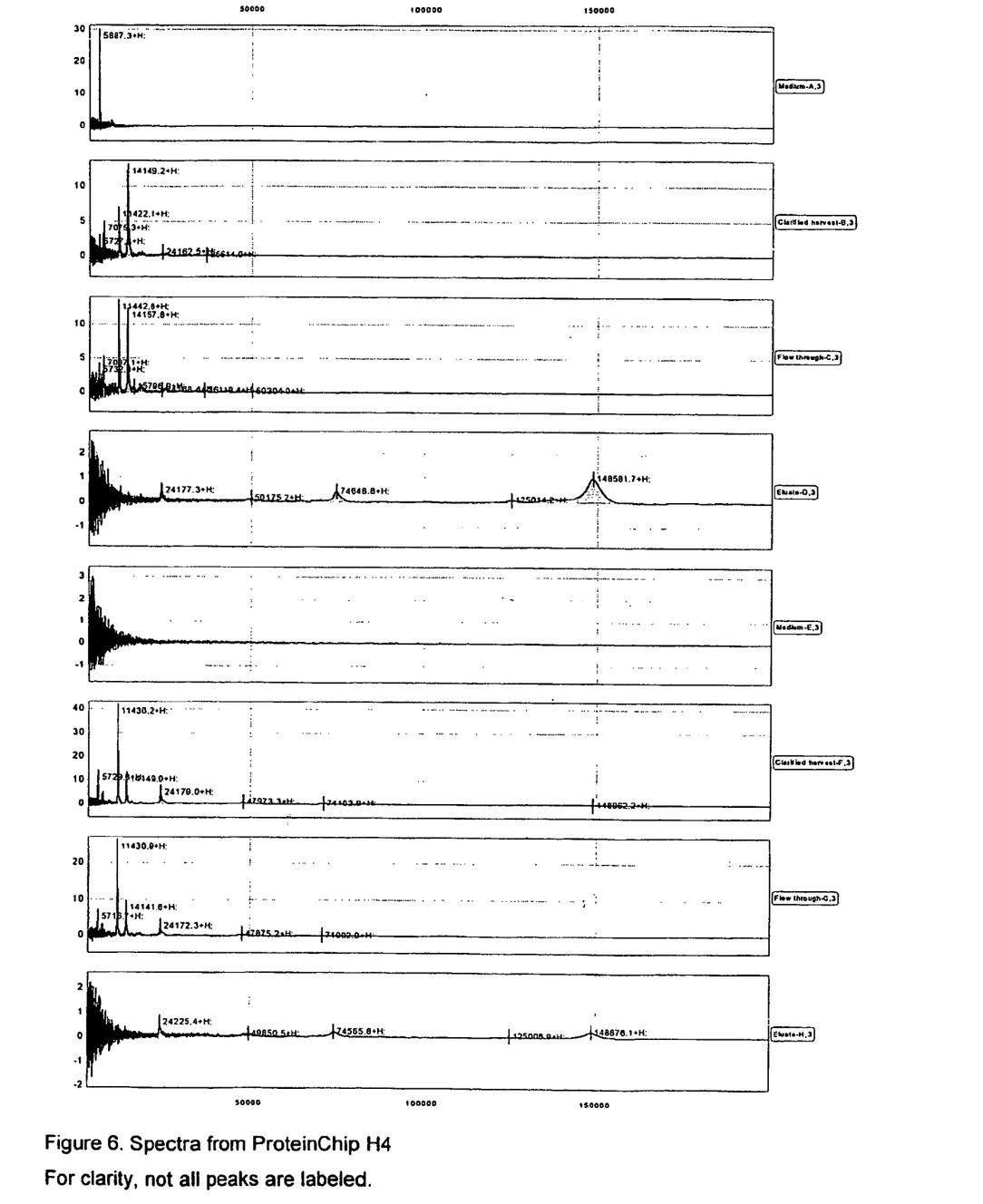
FIG. 6 shows spectra of ProteinChip H4. For clarity, not all peaks are labeled.

As can be concluded from the spectra and tables shown under 6.0, it is possible to detect individual contaminants with high sensitivity with the SELDI-TOF-MS technique (FIG. 5). Additionally, by comparing at least two intermediates from the purification process the removal of these contaminants can be followed. To further improve the coverage of the impurities, more different buffer conditions may be needed. Additionally, more impurities of a lower mass may be obtained using a lower laser intensity.

The results indicated in Table 3 clearly show the removal of contaminants during the purification of the recombinant IgG1 over a proteinA column.

More ideally, the removal can be shown when more purification steps were executed.

5.0 Literature

1 Jones, D. H., van Berkel, P. H. C., Logtenberg, T. and Bout, A., 2002, 'PER.C6 cell line for human antibody production.', Gen. 22, ed. May 15.
2 Jones, D. et al., 2003, 'High-level expression of recombinant IgG in the human cell line PER.C6.', Biotechnol. Prog. 19, 163-168.

6.0 Tables

TABLE 4

Properties of the peaks obtained on ProteinChip NP20(1).

| Spectrum Tag | Peak # | Substance Mass | Signal/Noise | MZArea |
|---|---|---|---|---|
| Medium (SPA)-E,3 | 1 | 2314.09 | 8.19 | 59.78 |
| Medium (SPA)-E,3 | 2 | 2394.13 | 11.67 | 156.99 |
| Medium (SPA)-E,3 | 3 | 2765.63 | 16.55 | 112.21 |
| Medium (SPA)-E,3 | 4 | 2835.09 | 13.10 | 134.18 |
| Medium (SPA)-E,3 | 5 | 2924.53 | 10.30 | 31.16 |
| Medium (SPA)-E,3 | 6 | 3010.59 | 13.72 | 165.44 |
| Medium (SPA)-E,3 | 7 | 3090.24 | 9.34 | 59.81 |
| Medium (SPA)-E,3 | 8 | 3175.96 | 7.84 | 15.28 |
| Medium (SPA)-E,3 | 9 | 3276.77 | 33.63 | 759.38 |
| Medium (SPA)-E,3 | 10 | 3426.94 | 13.16 | 127.12 |
| Medium (SPA)-E,3 | 11 | 3589.79 | 20.06 | 223.20 |
| Medium (SPA)-E,3 | 12 | 3772.22 | 12.87 | 160.02 |
| Medium (SPA)-E,3 | 13 | 3922.20 | 42.12 | 702.66 |
| Medium (SPA)-E,3 | 14 | 4079.61 | 10.23 | 34.48 |
| Medium (SPA)-E,3 | 15 | 4199.42 | 11.61 | 106.90 |
| Medium (SPA)-E,3 | 16 | 4361.65 | 9.09 | 34.64 |
| Medium (SPA)-E,3 | 17 | 5304.99 | 17.81 | 252.62 |
| Medium (SPA)-E,3 | 18 | 5464.59 | 7.93 | 60.46 |
| Medium (SPA)-E,3 | 19 | 5882.33 | 79.88 | 1737.02 |
| Medium (SPA)-E,3 | 20 | 6041.78 | 29.24 | 617.99 |
| Medium (SPA)-E,3 | 21 | 76281.29 | 2.69 | 8.70 |
| total area | | | | 5560.06 |
| % impurities | | | | N.A. |
| Clarified harvest (SPA)-F,3 | 1 | 2790.38 | 3.39 | 9.71 |
| Clarified harvest (SPA)-F,3 | 2 | 2830.94 | 3.26 | 9.68 |
| Clarified harvest (SPA)-F,3 | 3 | 2858.67 | 3.54 | 8.79 |
| Clarified harvest (SPA)-F,3 | 4 | 3276.84 | 10.14 | 339.68 |
| Clarified harvest (SPA)-F,3 | 5 | 3623.06 | 3.60 | 29.32 |
| Clarified harvest (SPA)-F,3 | 6 | 3933.88 | 5.49 | 150.39 |
| Clarified harvest (SPA)-F,3 | 7 | 4222.08 | 3.31 | 9.43 |
| Clarified harvest (SPA)-F,3 | 9 | 5709.98 | 6.28 | 247.72 |
| Clarified harvest (SPA)-F,3 | 11 | 6960.51 | 4.86 | 194.49 |
| Clarified harvest (SPA)-F,3 | 12 | 7090.48 | 4.82 | 209.67 |
| Clarified harvest (SPA)-F,3 | 14 | 8664.71 | 3.71 | 193.47 |
| Clarified harvest (SPA)-F,3 | 17 | 11416.38 | 19.22 | 1252.12 |
| Clarified harvest (SPA)-F,3 | 19 | 12095.45 | 2.54 | 112.74 |
| Clarified harvest (SPA)-F,3 | 20 | 13912.07 | 23.74 | 1286.60 |
| Clarified harvest (SPA)-F,3 | 21 | 15466.19 | 3.88 | 241.47 |
| Clarified harvest (SPA)-F,3 | 24 | 24128.32 | 51.47 | 633.01 |
| Clarified harvest (SPA)-F,3 | 25 | 33262.84 | 3.26 | 38.03 |
| Clarified harvest (SPA)-F,3 | 26 | 57018.90 | 3.39 | 16.32 |
| Clarified harvest (SPA)-F,3 | 27 | 62157.35 | 3.51 | 14.83 |
| Clarified harvest (SPA)-F,3 | 28 | 66439.13 | 3.57 | 16.31 |
| Clarified harvest (SPA)-F,3 | 29 | 74334.31 | 10.12 | 132.23 |
| Clarified harvest (SPA)-F,3 | 30 | 74966.20 | 7.43 | 0.00 |
| Clarified harvest (SPA)-F,3 | 31 | 83605.50 | 3.87 | 16.97 |
| Clarified harvest (SPA)-F,3 | 32 | 91687.99 | 3.97 | 23.08 |
| Clarified harvest (SPA)-F,3 | 33 | 94907.68 | 3.94 | 15.19 |
| Clarified harvest (SPA)-F,3 | 34 | 97667.12 | 3.31 | 17.71 |
| Clarified harvest (SPA)-F,3 | 35 | 110685.01 | 4.21 | 23.26 |
| Clarified harvest (SPA)-F,3 | 36 | 148476.77 | 23.89 | 425.31 |
| total area | | | | 4265.18 |
| total IgG | | | | 557.54 |
| % impurities | | | | 87 |
| Flow through proteinA (SPA)-G,3 | 1 | 2764.00 | 3.88 | 12.99 |
| Flow through proteinA (SPA)-G,3 | 2 | 2859.74 | 4.29 | 97.07 |
| Flow through proteinA (SPA)-G,3 | 3 | 2985.07 | 3.19 | 12.97 |
| Flow through proteinA (SPA)-G,3 | 4 | 3277.60 | 11.74 | 663.11 |
| Flow through proteinA (SPA)-G,3 | 5 | 3604.29 | 3.96 | 32.93 |
| Flow through proteinA (SPA)-G,3 | 6 | 3930.16 | 6.86 | 333.87 |
| Flow through proteinA (SPA)-G,3 | 7 | 5320.74 | 4.54 | 270.21 |
| Flow through proteinA (SPA)-G,3 | 8 | 5460.20 | 2.23 | 79.63 |
| Flow through proteinA (SPA)-G,3 | 9 | 5704.24 | 5.76 | 329.91 |
| Flow through proteinA (SPA)-G,3 | 10 | 5919.25 | 2.25 | 138.98 |
| Flow through proteinA (SPA)-G,3 | 11 | 6332.58 | 2.07 | 132.79 |
| Flow through proteinA (SPA)-G,3 | 12 | 6962.82 | 4.04 | 181.56 |
| Flow through proteinA (SPA)-G,3 | 13 | 7068.46 | 3.78 | 221.30 |
| Flow through proteinA (SPA)-G,3 | 16 | 8643.34 | 10.12 | 803.75 |
| Flow through proteinA (SPA)-G,3 | 17 | 9061.62 | 3.58 | 266.49 |

TABLE 4-continued

Properties of the peaks obtained on ProteinChip NP20(1).

| Spectrum Tag | Peak # | Substance Mass | Signal/Noise | MZArea |
|---|---|---|---|---|
| (SPA)-G,3 | | | | |
| Flow through proteinA (SPA)-G,3 | 18 | 9252.41 | 4.04 | 503.32 |
| Flow through proteinA (SPA)-G,3 | 22 | 10943.49 | 3.14 | 200.39 |
| Flow through proteinA (SPA)-G,3 | 23 | 11404.10 | 22.28 | 1804.41 |
| Flow through proteinA (SPA)-G,3 | 24 | 11808.19 | 5.28 | 438.03 |
| Flow through proteinA (SPA)-G,3 | 25 | 12067.62 | 3.27 | 195.23 |
| Flow through proteinA (SPA)-G,3 | 26 | 12673.36 | 3.54 | 450.38 |
| Flow through proteinA (SPA)-G,3 | 27 | 14117.23 | 20.48 | 1649.82 |
| Flow through proteinA (SPA)-G,3 | 28 | 15471.18 | 6.03 | 440.08 |
| Flow through proteinA (SPA)-G,3 | 29 | 16079.15 | 2.50 | 139.22 |
| Flow through proteinA (SPA)-G,3 | 30 | 16948.95 | 3.30 | 132.27 |
| Flow through proteinA (SPA)-G,3 | 31 | 17363.56 | 5.23 | 242.57 |
| Flow through proteinA (SPA)-G,3 | 33 | 24122.09 | 45.39 | 1035.70 |
| Flow through proteinA (SPA)-G,3 | 34 | 33319.38 | 4.89 | 0.00 |
| Flow through proteinA (SPA)-G,3 | 35 | 33638.74 | 4.31 | 0.00 |
| Flow through proteinA (SPA)-G,3 | 36 | 43198.62 | 3.68 | 89.27 |
| Flow through proteinA (SPA)-G,3 | 37 | 48027.33 | 5.44 | 112.84 |
| Flow through proteinA (SPA)-G,3 | 38 | 58447.15 | 4.67 | 78.67 |
| Flow through proteinA (SPA)-G,3 | 39 | 60529.84 | 4.45 | 67.52 |
| Flow through proteinA (SPA)-G,3 | 40 | 69511.32 | 4.38 | 83.96 |
| Flow through proteinA (SPA)-G,3 | 41 | 78129.68 | 3.71 | 50.26 |
| total area | | | | 7210.61 |
| % impurities | | | | N.A. |
| Eluate ProteinA (SPA)-H,3 | 3 | 24082.27 | 16.88 | 213.36 |
| Eluate ProteinA (SPA)-H,3 | 4 | 49568.37 | 7.63 | 93.81 |
| Eluate ProteinA (SPA)-H,3 | 5 | 62528.03 | 4.64 | 27.43 |
| Eluate ProteinA (SPA)-H,3 | 6 | 69252.85 | 3.87 | 22.78 |
| Eluate ProteinA (SPA)-H,3 | 7 | 74295.17 | 48.93 | 723.83 |
| Eluate ProteinA (SPA)-H,3 | 8 | 100909.85 | 9.54 | 154.02 |
| Eluate ProteinA (SPA)-H,3 | 9 | 124621.82 | 8.98 | 140.59 |
| Eluate ProteinA (SPA)-H,3 | 10 | 136473.23 | 9.63 | 0.00 |
| Eluate ProteinA (SPA)-H,3 | 11 | 141315.86 | 7.93 | 0.00 |
| Eluate ProteinA (SPA)-H,3 | 12 | 148617.17 | 108.45 | 2440.16 |
| total area | | | | 3815.99 |
| total IgG | | | | 3257.80 |
| % impurities | | | | 15 |

TABLE 5

ProteinChip NP20(2)

| Spectrum Tag | Peak # | Substance Mass | Signal/Noise | MZArea |
|---|---|---|---|---|
| Medium-A,3 | 1 | 5860.39 | 364.88 | 6633.61 |
| Medium-A,3 | 2 | 9193.41 | 84.32 | 6687.72 |
| total area | | | | 13321.32 |
| % impurities | | | | N.A. |
| C en C-B,3 | 1 | 5710.56 | 4.39 | 59.16 |
| C en C-B,3 | 2 | 7042.05 | 8.50 | 425.65 |
| C en C-B,3 | 3 | 11332.92 | 10.65 | 978.26 |
| C en C-B,3 | 4 | 11791.28 | 11.39 | 1935.32 |
| C en C-B,3 | 5 | 14010.33 | 26.47 | 4190.09 |
| C en C-B,3 | 6 | 16888.37 | 6.91 | 444.55 |
| C en C-B,3 | 7 | 17910.82 | 5.09 | 456.77 |
| C en C-B,3 | 8 | 23978.65 | 32.32 | 2851.85 |
| C en C-B,3 | 9 | 36858.87 | 2.37 | 57.53 |
| C en C-B,3 | 10 | 47766.40 | 5.69 | 399.19 |
| C en C-B,3 | 11 | 70595.87 | 4.70 | 225.95 |
| C en C-B,3 | 12 | 74067.64 | 4.41 | 149.79 |
| C en C-B,3 | 13 | 147954.48 | 12.75 | 647.51 |
| total area | | | | 12821.62 |
| total IgG | | | | 797.30 |
| % impurities | | | | 94 |
| Flow through-C,3 | 1 | 7062.05 | 5.20 | 138.52 |
| Flow through-C,3 | 2 | 8455.61 | 4.08 | 201.00 |
| Flow through-C,3 | 3 | 9237.37 | 3.30 | 319.58 |
| Flow through-C,3 | 4 | 11793.03 | 12.77 | 1797.05 |
| Flow through-C,3 | 5 | 13814.21 | 18.77 | 0.00 |
| Flow through-C,3 | 6 | 14021.30 | 21.18 | 0.00 |
| Flow through-C,3 | 7 | 16891.03 | 12.54 | 964.29 |
| Flow through-C,3 | 8 | 17992.06 | 10.69 | 1309.05 |
| Flow through-C,3 | 9 | 23996.07 | 25.30 | 1200.81 |
| Flow through-C,3 | 10 | 24949.28 | 16.76 | 0.00 |
| Flow through-C,3 | 11 | 29010.75 | 8.23 | 843.93 |
| Flow through-C,3 | 12 | 36891.66 | 10.57 | 778.70 |
| Flow through-C,3 | 13 | 42714.39 | 9.21 | 483.74 |
| Flow through-C,3 | 14 | 47411.80 | 11.12 | 442.83 |
| Flow through-C,3 | 15 | 70536.15 | 21.00 | 732.48 |
| total area | | | | 8872.45 |
| Eluate-D,3 | 5 | 62626.76 | 5.85 | 0.00 |
| Eluate-D,3 | 6 | 74181.35 | 50.93 | 1127.73 |
| Eluate-D,3 | 7 | 100857.20 | 7.72 | 308.86 |
| Eluate-D,3 | 8 | 124659.03 | 20.69 | 639.50 |
| Eluate-D,3 | 9 | 137791.90 | 26.99 | 0.00 |
| Eluate-D,3 | 10 | 148104.09 | 208.42 | 4642.80 |
| total area | | | | 6718.89 |
| total IgG | | | | 5770.52 |
| % impurities | | | | 14 |
| Medium-E,3 | 1 | 5891.04 | 20.04 | 231.84 |
| total area | | | | 231.84 |
| Clarified harvest-F,3 | 1 | 3064.36 | 8.81 | 42.14 |
| Clarified harvest-F,3 | 2 | 4412.23 | 7.56 | 18.14 |
| Clarified harvest-F,3 | 3 | 11726.80 | 4.01 | 85.49 |
| Clarified harvest-F,3 | 4 | 14029.33 | 6.25 | 239.54 |
| Clarified harvest-F,3 | 5 | 17955.27 | 5.90 | 183.14 |
| Clarified harvest-F,3 | 6 | 23953.97 | 5.41 | 275.83 |
| Clarified harvest-F,3 | 7 | 25015.06 | 5.68 | 296.51 |
| Clarified harvest-F,3 | 8 | 147834.60 | 5.91 | 101.90 |
| total area | | | | 1242.69 |
| total IgG | | | | 101.90 |
| % impurities | | | | 92 |
| Flow through-G,3 | 1 | 6343.01 | 4.78 | 15.33 |
| Flow through-G,3 | 2 | 11707.14 | 7.54 | 399.20 |
| Flow through-G,3 | 3 | 13799.53 | 7.16 | 793.41 |
| Flow through-G,3 | 4 | 17939.66 | 11.95 | 789.49 |
| Flow through-G,3 | 5 | 24927.50 | 9.66 | 968.69 |
| Flow through-G,3 | 6 | 35795.86 | 22.02 | 1215.47 |
| Flow through-G,3 | 7 | 42594.44 | 14.12 | 745.16 |
| Flow through-G,3 | 8 | 50977.25 | 6.45 | 84.33 |
| Flow through-G,3 | 9 | 62938.72 | 5.45 | 127.72 |
| total area | | | | 5138.80 |
| Eluate-H,3 | 1 | 23891.50 | 9.19 | 398.69 |
| Eluate-H,3 | 2 | 49295.07 | 9.69 | 330.88 |
| Eluate-H,3 | 3 | 74063.97 | 65.46 | 1254.34 |
| Eluate-H,3 | 4 | 99316.11 | 9.70 | 342.31 |
| Eluate-H,3 | 5 | 124318.75 | 28.14 | 947.02 |

TABLE 5-continued

ProteinChip NP20(2)

| Spectrum Tag | Peak # | Substance. Mass | Signal/ Noise | MZArea |
|---|---|---|---|---|
| Eluate-H,3 | 6 | 136343.78 | 33.38 | 0.00 |
| Eluate-H,3 | 7 | 147838.98 | 306.08 | 6394.98 |
| total area | | | | 9668.21 |
| total IgG | | | | 7980.20 |
| % impurities | | | | 17 |

TABLE 6

ProteinChip SAX2

| Spectrum Tag | Peak # | Substance. Mass | Signal/ Noise | MZArea |
|---|---|---|---|---|
| Medium-A,2 | 1 | 2713.52 | 26.62 | 22.27 |
| Medium-A,2 | 2 | 2778.72 | 21.91 | 20.02 |
| Medium-A,2 | 3 | 2900.23 | 59.47 | 312.13 |
| Medium-A,2 | 4 | 2987.94 | 31.65 | 89.55 |
| Medium-A,2 | 5 | 3090.50 | 26.52 | 47.54 |
| Medium-A,2 | 6 | 3211.08 | 21.60 | 18.64 |
| Medium-A,2 | 7 | 3224.21 | 23.34 | 10.49 |
| Medium-A,2 | 8 | 3308.27 | 128.33 | 1177.16 |
| Medium-A,2 | 9 | 3412.93 | 18.75 | 15.33 |
| Medium-A,2 | 10 | 3421.61 | 20.15 | 20.46 |
| Medium-A,2 | 11 | 3639.36 | 97.37 | 584.61 |
| Medium-A,2 | 12 | 3717.15 | 39.82 | 139.21 |
| Medium-A,2 | 13 | 3813.36 | 101.17 | 872.13 |
| Medium-A,2 | 14 | 3959.79 | 188.07 | 1775.78 |
| Medium-A,2 | 15 | 4126.10 | 42.36 | 175.18 |
| Medium-A,2 | 16 | 4213.61 | 96.53 | 0.00 |
| Medium-A,2 | 17 | 4275.04 | 33.09 | 23.51 |
| Medium-A,2 | 18 | 4340.21 | 25.21 | 36.12 |
| Medium-A,2 | 19 | 4377.77 | 86.55 | 625.19 |
| Medium-A,2 | 20 | 4459.46 | 23.02 | 18.67 |
| Medium-A,2 | 21 | 4496.85 | 36.45 | 170.60 |
| Medium-A,2 | 22 | 4621.64 | 22.00 | 79.15 |
| Medium-A,2 | 23 | 4780.36 | 9.28 | 11.45 |
| Medium-A,2 | 24 | 5087.29 | 17.97 | 27.89 |
| Medium-A,2 | 25 | 5197.47 | 20.71 | 44.35 |
| Medium-A,2 | 26 | 5241.93 | 13.83 | 15.52 |
| Medium-A,2 | 27 | 5314.44 | 160.99 | 1280.63 |
| Medium-A,2 | 28 | 5440.62 | 57.36 | 560.11 |
| Medium-A,2 | 29 | 5663.81 | 3.84 | 1.12 |
| Medium-A,2 | 30 | 5678.76 | 25.76 | 140.85 |
| Medium-A,2 | 31 | 5844.07 | 444.92 | 6355.35 |
| Medium-A,2 | 32 | 6047.32 | 181.90 | 0.00 |
| Medium-A,2 | 33 | 6247.31 | 11.32 | 11.14 |
| Medium-A,2 | 34 | 6283.35 | 13.40 | 14.86 |
| Medium-A,2 | 35 | 6530.00 | 8.38 | 17.30 |
| Medium-A,2 | 36 | 8999.56 | 73.19 | 5268.68 |
| total area | | | | 19982.97 |
| Clarified harvestl-B,2 | 1 | 2590.68 | 15.35 | 31.09 |
| Clarified harvestl-B,2 | 2 | 2716.13 | 18.43 | 98.62 |
| Clarified harvestl-B,2 | 3 | 2776.71 | 12.11 | 11.41 |
| Clarified harvestl-B,2 | 4 | 2832.17 | 34.92 | 352.50 |
| Clarified harvestl-B,2 | 5 | 2897.29 | 39.27 | 565.32 |
| Clarified harvestl-B,2 | 6 | 2978.07 | 23.28 | 170.27 |
| Clarified harvestl-B,2 | 7 | 3062.36 | 26.97 | 333.91 |
| Clarified harvestl-B,2 | 8 | 3157.60 | 18.57 | 153.61 |
| Clarified harvestl-B,2 | 9 | 3163.38 | 19.60 | 55.00 |
| Clarified harvestl-B,2 | 10 | 3211.03 | 8.87 | 11.34 |
| Clarified harvestl-B,2 | 11 | 3314.21 | 107.97 | 2170.66 |
| Clarified harvestl-B,2 | 12 | 3460.09 | 31.02 | 343.71 |
| Clarified harvestl-B,2 | 13 | 3629.10 | 31.94 | 374.12 |
| Clarified harvestl-B,2 | 14 | 3818.06 | 22.57 | 401.18 |
| Clarified harvestl-B,2 | 15 | 3960.99 | 67.52 | 1328.45 |
| Clarified harvestl-B,2 | 16 | 4238.70 | 12.92 | 188.75 |
| Clarified harvestl-B,2 | 17 | 4398.02 | 16.79 | 201.38 |
| Clarified harvestl-B,2 | 18 | 4969.33 | 9.86 | 225.19 |
| Clarified harvestl-B,2 | 19 | 5324.37 | 30.81 | 707.91 |

TABLE 6-continued

ProteinChip SAX2

| Spectrum Tag | Peak # | Substance. Mass | Signal/ Noise | MZArea |
|---|---|---|---|---|
| Clarified harvestl-B,2 | 20 | 5461.67 | 13.14 | 317.90 |
| Clarified harvestl-B,2 | 21 | 5711.92 | 7.56 | 114.01 |
| Clarified harvestl-B,2 | 22 | 5902.53 | 20.93 | 531.52 |
| Clarified harvestl-B,2 | 23 | 6008.25 | 7.48 | 156.21 |
| Clarified harvestl-B,2 | 24 | 8012.39 | 6.27 | 171.74 |
| Clarified harvestl-B,2 | 25 | 8591.82 | 7.43 | 258.64 |
| Clarified harvestl-B,2 | 26 | 9015.57 | 14.76 | 2135.01 |
| Clarified harvestl-B,2 | 27 | 9986.92 | 4.39 | 179.81 |
| Clarified harvestl-B,2 | 28 | 10525.99 | 7.43 | 754.33 |
| Clarified harvestl-B,2 | 29 | 11739.92 | 26.33 | 1283.06 |
| Clarified harvestl-B,2 | 30 | 11961.13 | 24.46 | 1556.40 |
| Clarified harvestl-B,2 | 31 | 16775.53 | 14.58 | 363.70 |
| Clarified harvestl-B,2 | 32 | 17197.99 | 12.69 | 427.99 |
| Clarified harvestl-B,2 | 33 | 17904.06 | 7.08 | 318.49 |
| Clarified harvestl-B,2 | 34 | 19802.16 | 3.10 | 92.61 |
| Clarified harvestl-B,2 | 35 | 23900.54 | 141.16 | 3796.78 |
| Clarified harvestl-B,2 | 36 | 47691.60 | 26.29 | 375.64 |
| Clarified harvestl-B,2 | 37 | 68213.89 | 6.04 | 151.62 |
| Clarified harvestl-B,2 | 38 | 73916.24 | 33.54 | 379.67 |
| Clarified harvestl-B,2 | 39 | 147550.06 | 59.11 | 908.81 |
| total area | | | | 21998.33 |
| total IgG | | | | 1288.48 |
| % impurities | | | | 94 |
| FLow through-C,2 | 1 | 2906.70 | 11.55 | 540.98 |
| FLow through-C,2 | 2 | 3317.05 | 21.51 | 1621.86 |
| FLow through-C,2 | 3 | 3468.01 | 7.15 | 476.61 |
| FLow through-C,2 | 4 | 3646.93 | 10.09 | 479.39 |
| FLow through-C,2 | 5 | 3814.15 | 8.90 | 643.06 |
| FLow through-C,2 | 6 | 3960.44 | 18.89 | 1344.77 |
| FLow through-C,2 | 7 | 4121.23 | 4.04 | 58.85 |
| FLow through-C,2 | 8 | 4227.84 | 4.44 | 83.42 |
| FLow through-C,2 | 9 | 4388.70 | 7.13 | 158.78 |
| FLow through-C,2 | 10 | 5318.40 | 12.91 | 995.17 |
| FLow through-C,2 | 11 | 5446.43 | 5.42 | 490.38 |
| FLow through-C,2 | 12 | 5716.62 | 3.83 | 256.65 |
| FLow through-C,2 | 13 | 5906.83 | 9.42 | 786.31 |
| FLow through-C,2 | 14 | 6035.28 | 3.23 | 225.37 |
| FLow through-C,2 | 15 | 7998.31 | 2.35 | 235.50 |
| FLow through-C,2 | 16 | 8620.11 | 3.31 | 386.70 |
| FLow through-C,2 | 17 | 9007.51 | 11.02 | 5192.99 |
| FLow through-C,2 | 18 | 9978.93 | 3.90 | 304.91 |
| FLow through-C,2 | 19 | 10541.24 | 11.09 | 2079.66 |
| FLow through-C,2 | 20 | 11740.26 | 31.34 | 3241.77 |
| FLow through-C,2 | 21 | 11974.79 | 25.62 | 3109.06 |
| FLow through-C,2 | 22 | 16777.65 | 26.38 | 1392.59 |
| FLow through-C,2 | 23 | 17202.51 | 22.70 | 1669.60 |
| FLow through-C,2 | 24 | 17889.61 | 8.36 | 0.00 |
| FLow through-C,2 | 25 | 19789.91 | 5.36 | 375.33 |
| FLow through-C,2 | 26 | 23904.15 | 198.81 | 7343.86 |
| FLow through-C,2 | 27 | 28769.40 | 12.81 | 1623.63 |
| FLow through-C,2 | 28 | 42582.78 | 15.32 | 629.36 |
| FLow through-C,2 | 29 | 47670.67 | 39.78 | 1136.63 |
| FLow through-C,2 | 30 | 58132.37 | 8.99 | 638.85 |
| FLow through-C,2 | 31 | 70606.68 | 13.09 | 933.51 |
| total area | | | | 38455.56 |
| Eluate-D,2 | 1 | 2576.16 | 34.15 | 16.23 |
| Eluate-D,2 | 2 | 2582.81 | 47.05 | 20.21 |
| Eluate-D,2 | 3 | 2593.40 | 43.89 | 16.72 |
| Eluate-D,2 | 4 | 2671.64 | 44.61 | 24.51 |
| Eluate-D,2 | 5 | 2695.34 | 33.21 | 11.49 |
| Eluate-D,2 | 6 | 2719.63 | 35.97 | 21.73 |
| Eluate-D,2 | 7 | 2752.66 | 33.35 | 14.73 |
| Eluate-D,2 | 8 | 2867.66 | 35.21 | 18.70 |
| Eluate-D,2 | 9 | 2899.41 | 28.33 | 14.29 |
| Eluate-D,2 | 10 | 3356.51 | 20.30 | 11.18 |
| Eluate-D,2 | 11 | 3753.28 | 20.69 | 13.04 |
| Eluate-D,2 | 12 | 3798.45 | 21.04 | 5.91 |
| Eluate-D,2 | 13 | 3969.23 | 25.29 | 7.68 |
| Eluate-D,2 | 14 | 4190.38 | 22.65 | 5.10 |
| Eluate-D,2 | 15 | 4397.72 | 12.18 | 6.29 |
| Eluate-D,2 | 16 | 6055.07 | 3.59 | 3.74 |
| Eluate-D,2 | 17 | 24089.68 | 2.91 | 35.65 |

TABLE 6-continued

ProteinChip SAX2

| Spectrum Tag | Peak # | Substance. Mass | Signal/Noise | MZArea |
|---|---|---|---|---|
| Eluate-D,2 | 18 | 49537.08 | 5.31 | 110.61 |
| Eluate-D,2 | 19 | 74196.14 | 17.91 | 257.83 |
| Eluate-D,2 | 20 | 148555.69 | 36.74 | 570.95 |
| total area | | | | 1186.60 |
| total IgG | | | | 939.39 |
| % impurities | | | | 21 |
| Medium-E,2 | 1 | 3601.76 | 129.52 | 488.87 |
| Medium-E,2 | 2 | 3782.73 | 165.97 | 820.31 |
| Medium-E,2 | 3 | 3929.78 | 267.89 | 1632.07 |
| Medium-E,2 | 4 | 4386.72 | 131.96 | 701.40 |
| Medium-E,2 | 5 | 5319.69 | 343.87 | 1513.28 |
| Medium-E,2 | 6 | 5452.61 | 127.15 | 729.64 |
| Medium-E,2 | 7 | 5718.22 | 63.99 | 200.03 |
| Medium-E,2 | 8 | 5916.87 | 214.28 | 1145.58 |
| Medium-E,2 | 9 | 9220.66 | 208.58 | 7503.49 |
| Medium-E,2 | 10 | 13685.69 | 6.54 | 77.91 |
| total area | | | | 14812.58 |
| Clarified harvest-F,2 | 1 | 3272.89 | 121.69 | 2097.31 |
| Clarified harvest-F,2 | 2 | 3599.63 | 43.04 | 497.14 |
| Clarified harvest-F,2 | 3 | 3762.00 | 26.94 | 579.32 |
| Clarified harvest-F,2 | 4 | 3935.99 | 93.42 | 1403.82 |
| Clarified harvest-F,2 | 5 | 5318.92 | 48.22 | 906.76 |
| Clarified harvest-F,2 | 6 | 5440.03 | 19.16 | 496.65 |
| Clarified harvest-F,2 | 7 | 5915.51 | 20.63 | 375.79 |
| Clarified harvest-F,2 | 8 | 8477.28 | 7.87 | 296.99 |
| Clarified harvest-F,2 | 9 | 9078.72 | 30.21 | 3635.94 |
| Clarified harvest-F,2 | 10 | 10612.09 | 19.92 | 1295.91 |
| Clarified harvest-F,2 | 11 | 11541.35 | 7.64 | 268.91 |
| Clarified harvest-F,2 | 12 | 13035.18 | 2.29 | 70.02 |
| Clarified harvest-F,2 | 13 | 16933.20 | 25.38 | 611.22 |
| Clarified harvest-F,2 | 14 | 17369.59 | 18.82 | 497.21 |
| Clarified harvest-F,2 | 15 | 20680.34 | 4.52 | 72.05 |
| Clarified harvest-F,2 | 16 | 23296.85 | 7.47 | 347.37 |
| Clarified harvest-F,2 | 17 | 24950.67 | 11.17 | 388.56 |
| Clarified harvest-F,2 | 18 | 28058.54 | 7.81 | 948.93 |
| Clarified harvest-F,2 | 19 | 33191.09 | 5.12 | 165.72 |
| Clarified harvest-F,2 | 20 | 36865.60 | 5.49 | 138.16 |
| Clarified harvest-F,2 | 21 | 43107.08 | 11.34 | 258.57 |
| Clarified harvest-F,2 | 22 | 46810.80 | 7.55 | 145.45 |
| Clarified harvest-F,2 | 23 | 70815.42 | 14.96 | 292.35 |
| Clarified harvest-F,2 | 24 | 149936.98 | 6.83 | 93.13 |
| total area | | | | 15883.28 |
| total IgG | | | | 530.93 |
| % impurities | | | | 97 |
| Flow through-G,2 | 1 | 3264.54 | 34.52 | 1324.66 |
| Flow through-G,2 | 2 | 3594.31 | 19.09 | 591.08 |
| Flow through-G,2 | 3 | 3786.43 | 23.15 | 871.88 |
| Flow through-G,2 | 4 | 3929.11 | 48.81 | 1837.82 |
| Flow through-G,2 | 5 | 5312.77 | 37.12 | 1402.01 |
| Flow through-G,2 | 6 | 5922.88 | 15.11 | 658.82 |
| Flow through-G,2 | 7 | 8455.26 | 6.80 | 468.09 |
| Flow through-G,2 | 8 | 9225.16 | 29.96 | 6415.58 |
| Flow through-G,2 | 9 | 10606.91 | 23.79 | 2763.20 |
| Flow through-G,2 | 10 | 11775.39 | 7.95 | 656.69 |
| Flow through-G,2 | 11 | 12067.31 | 8.63 | 677.17 |
| Flow through-G,2 | 12 | 12960.65 | 2.50 | 150.00 |
| Flow through-G,2 | 13 | 16921.27 | 39.10 | 1428.76 |
| Flow through-G,2 | 14 | 17364.57 | 25.51 | 1286.58 |
| Flow through-G,2 | 15 | 20859.42 | 4.54 | 485.68 |
| Flow through-G,2 | 16 | 23280.42 | 7.52 | 740.08 |
| Flow through-G,2 | 17 | 24977.53 | 12.94 | 1204.05 |
| Flow through-G,2 | 18 | 28895.75 | 16.22 | 2539.96 |
| Flow through-G,2 | 19 | 33269.63 | 7.74 | 310.53 |
| Flow through-G,2 | 20 | 36705.26 | 5.55 | 170.61 |
| Flow through-G,2 | 21 | 42842.61 | 20.64 | 435.44 |
| Flow through-G,2 | 22 | 46646.95 | 11.17 | 274.07 |
| Flow through-G,2 | 23 | 70706.80 | 15.74 | 331.82 |
| total area | | | | 27024.59 |
| Eluate-H,2 | 1 | 5435.07 | 22.37 | 95.27 |
| Eluate-H,2 | 2 | 149534.16 | 8.73 | 192.16 |
| total area | | | | 287.43 |
| total IgG | | | | 192.16 |

TABLE 7

ProteinChip WCX2

| Spectrum Tag | Peak # | Substance. Mass | Signal/Noise | MZArea |
|---|---|---|---|---|
| Medium-A,3 | 1 | 4943.69 | 21.16 | 541.72 |
| Medium-A,3 | 2 | 5099.74 | 16.43 | 0.00 |
| Medium-A,3 | 3 | 5235.82 | 26.93 | 521.62 |
| Medium-A,3 | 4 | 5562.50 | 37.31 | 863.22 |
| Medium-A,3 | 5 | 5876.07 | 101.25 | 4512.01 |
| Medium-A,3 | 6 | 6077.45 | 96.20 | 1364.67 |
| Medium-A,3 | 7 | 6305.33 | 28.99 | 0.00 |
| Medium-A,3 | 8 | 6539.47 | 23.11 | 0.00 |
| Medium-A,3 | 9 | 7094.18 | 9.25 | 48.23 |
| Medium-A,3 | 10 | 9179.78 | 182.37 | 17535.64 |
| Medium-A,3 | 11 | 63411.41 | 4.93 | 46.97 |
| total area | | | | 25434.09 |
| % impurities | | | | n.a. |
| Clarified Harvest-B,3 | 1 | 5715.45 | 13.91 | 725.75 |
| Clarified Harvest-B,3 | 2 | 5922.93 | 9.86 | 399.69 |
| Clarified Harvest-B,3 | 3 | 6283.85 | 9.27 | 832.91 |
| Clarified Harvest-B,3 | 4 | 7049.43 | 28.48 | 1693.78 |
| Clarified Harvest-B,3 | 5 | 7456.76 | 8.16 | 266.59 |
| Clarified Harvest-B,3 | 6 | 7724.86 | 12.19 | 673.46 |
| Clarified Harvest-B,3 | 7 | 8016.99 | 7.15 | 706.98 |
| Clarified Harvest-B,3 | 8 | 8599.41 | 73.71 | 6246.24 |
| Clarified Harvest-B,3 | 9 | 9183.21 | 23.52 | 4214.18 |
| Clarified Harvest-B,3 | 10 | 10011.10 | 19.14 | 1015.12 |
| Clarified Harvest-B,3 | 11 | 10544.82 | 18.45 | 1165.61 |
| Clarified Harvest-B,3 | 12 | 10886.60 | 9.17 | 508.97 |
| Clarified Harvest-B,3 | 13 | 11330.29 | 118.08 | 9622.04 |
| Clarified Harvest-B,3 | 14 | 11528.63 | 26.60 | 0.00 |
| Clarified Harvest-B,3 | 15 | 11764.22 | 61.95 | 4639.09 |
| Clarified Harvest-B,3 | 16 | 11987.44 | 26.65 | 0.00 |
| Clarified Harvest-B,3 | 17 | 12473.29 | 34.64 | 3525.59 |
| Clarified Harvest-B,3 | 18 | 12674.07 | 12.35 | 0.00 |
| Clarified Harvest-B,3 | 19 | 12929.29 | 6.94 | 0.00 |
| Clarified Harvest-B,3 | 20 | 13392.82 | 13.32 | 0.00 |
| Clarified Harvest-B,3 | 21 | 13396.97 | 13.45 | 0.00 |
| Clarified Harvest-B,3 | 22 | 13805.90 | 105.49 | 0.00 |
| Clarified Harvest-B,3 | 23 | 14025.27 | 112.85 | 11264.36 |
| Clarified Harvest-B,3 | 24 | 14223.45 | 28.29 | 0.00 |
| Clarified Harvest-B,3 | 25 | 14439.61 | 10.70 | 0.00 |
| Clarified Harvest-B,3 | 26 | 15344.97 | 32.97 | 3045.22 |
| Clarified Harvest-B,3 | 27 | 15988.13 | 13.72 | 991.12 |
| Clarified Harvest-B,3 | 28 | 16838.12 | 7.17 | 474.69 |
| Clarified Harvest-B,3 | 29 | 17239.90 | 10.31 | 703.53 |
| Clarified Harvest-B,3 | 30 | 17919.10 | 8.09 | 1154.77 |
| Clarified Harvest-B,3 | 31 | 23948.65 | 206.17 | 19847.70 |
| Clarified Harvest-B,3 | 32 | 24785.44 | 53.00 | 0.00 |
| Clarified Harvest-B,3 | 33 | 32022.92 | 12.57 | 0.00 |
| Clarified Harvest-B,3 | 34 | 33012.67 | 17.39 | 952.02 |
| Clarified Harvest-B,3 | 35 | 35783.06 | 8.66 | 0.00 |
| Clarified Harvest-B,3 | 36 | 37867.01 | 12.64 | 447.40 |
| Clarified Harvest-B,3 | 37 | 42635.93 | 20.51 | 506.52 |
| Clarified Harvest-B,3 | 38 | 47663.57 | 52.89 | 1345.62 |
| Clarified Harvest-B,3 | 39 | 51916.52 | 18.01 | 535.20 |
| Clarified Harvest-B,3 | 40 | 56840.47 | 20.73 | 322.56 |

TABLE 7-continued

ProteinChip WCX2

| Spectrum Tag | Peak # | Substance. Mass | Signal/ Noise | MZArea |
|---|---|---|---|---|
| Clarified Harvest-B,3 | 41 | 67741.44 | 14.04 | 0.00 |
| Clarified Harvest-B,3 | 42 | 73957.94 | 11.38 | 361.65 |
| Clarified Harvest-B,3 | 43 | 81693.83 | 7.84 | 494.99 |
| Clarified Harvest-B,3 | 44 | 96394.63 | 5.40 | 118.99 |
| Clarified Harvest-B,3 | 45 | 116691.70 | 6.01 | 88.41 |
| Clarified Harvest-B,3 | 46 | 123475.71 | 6.10 | 178.61 |
| Clarified Harvest-B,3 | 47 | 136406.73 | 6.66 | 0.00 |
| Clarified Harvest-B,3 | 48 | 147976.64 | 74.31 | 2140.44 |
| total area | | | | 81209.80 |
| total IgG | | | | 2502.09 |
| % impurities | | | | 97 |
| Flow through-C,3 | 1 | 7049.05 | 17.62 | 1853.02 |
| Flow through-C,3 | 2 | 8608.92 | 50.69 | 6299.60 |
| Flow through-C,3 | 3 | 9183.42 | 32.56 | 6902.11 |
| Flow through-C,3 | 4 | 9536.60 | 7.75 | 0.00 |
| Flow through-C,3 | 5 | 10007.14 | 36.19 | 1830.36 |
| Flow through-C,3 | 6 | 10547.40 | 34.32 | 1836.52 |
| Flow through-C,3 | 7 | 10676.81 | 15.87 | 0.00 |
| Flow through-C,3 | 8 | 10875.14 | 22.41 | 1140.98 |
| Flow through-C,3 | 9 | 11327.10 | 107.98 | 7648.68 |
| Flow through-C,3 | 10 | 11521.66 | 26.09 | 0.00 |
| Flow through-C,3 | 11 | 11766.73 | 88.45 | 6602.62 |
| Flow through-C,3 | 12 | 11979.21 | 38.29 | 0.00 |
| Flow through-C,3 | 13 | 12337.45 | 60.00 | 0.00 |
| Flow through-C,3 | 14 | 12465.97 | 103.53 | 0.00 |
| Flow through-C,3 | 15 | 12666.90 | 34.68 | 0.00 |
| Flow through-C,3 | 16 | 12914.30 | 15.43 | 0.00 |
| Flow through-C,3 | 17 | 13801.13 | 94.17 | 7009.16 |
| Flow through-C,3 | 18 | 14023.22 | 98.23 | 6887.76 |
| Flow through-C,3 | 19 | 14187.30 | 20.72 | 0.00 |
| Flow through-C,3 | 20 | 14454.40 | 7.84 | 0.00 |
| Flow through-C,3 | 21 | 14914.67 | 10.87 | 504.37 |
| Flow through-C,3 | 22 | 15343.88 | 43.77 | 2911.98 |
| Flow through-C,3 | 23 | 15983.25 | 31.17 | 1987.64 |
| Flow through-C,3 | 24 | 16845.93 | 7.89 | 0.00 |
| Flow through-C,3 | 25 | 17239.56 | 24.17 | 1624.72 |
| Flow through-C,3 | 26 | 17918.88 | 22.92 | 3363.35 |
| Flow through-C,3 | 27 | 23948.33 | 278.14 | 23034.55 |
| Flow through-C,3 | 28 | 24786.75 | 84.96 | 0.00 |
| Flow through-C,3 | 29 | 29454.37 | 17.55 | 3554.96 |
| Flow through-C,3 | 30 | 32009.27 | 23.20 | 999.07 |
| Flow through-C,3 | 31 | 33027.38 | 20.10 | 0.00 |
| Flow through-C,3 | 32 | 36368.20 | 16.44 | 1603.35 |
| Flow through-C,3 | 33 | 42639.38 | 37.52 | 1967.44 |
| Flow through-C,3 | 34 | 47712.12 | 50.72 | 2476.43 |
| Flow through-C,3 | 35 | 51989.03 | 15.72 | 555.70 |
| Flow through-C,3 | 36 | 56849.64 | 28.46 | 1714.27 |
| Flow through-C,3 | 37 | 68268.14 | 22.15 | 2671.25 |
| Flow through-C,3 | 38 | 81887.83 | 9.91 | 710.51 |
| Flow through-C,3 | 39 | 116355.19 | 8.73 | 316.14 |
| total area | | | | 98006.54 |
| % impurities | | | | n.a. |
| Eluate-D,3 | 1 | 10264.26 | 5.77 | 143.12 |
| Eluate-D,3 | 2 | 10701.90 | 5.60 | 140.34 |
| Eluate-D,3 | 3 | 12003.09 | 3.52 | 72.02 |
| Eluate-D,3 | 4 | 13266.11 | 2.04 | 8.04 |
| Eluate-D,3 | 5 | 23950.73 | 17.61 | 881.09 |
| Eluate-D,3 | 6 | 49326.92 | 10.53 | 356.51 |
| Eluate-D,3 | 7 | 74022.16 | 43.90 | 879.77 |
| Eluate-D,3 | 8 | 124216.40 | 15.91 | 449.23 |
| Eluate-D,3 | 9 | 136681.22 | 19.32 | 0.00 |
| Eluate-D,3 | 10 | 147862.22 | 186.72 | 3769.38 |
| total area | | | | 6699.49 |
| total IgG | | | | 5005.65 |
| % impurities | | | | 25.28 |
| Medium-E,3 | 1 | 4049.65 | 12.75 | 47.08 |
| Medium-E,3 | 2 | 4284.42 | 12.91 | 110.64 |
| Medium-E,3 | 3 | 5349.83 | 9.15 | 18.85 |
| Medium-E,3 | 4 | 5889.82 | 12.45 | 148.65 |
| Medium-E,3 | 5 | 6438.94 | 7.43 | 15.31 |
| Medium-E,3 | 6 | 9247.11 | 4.85 | 33.39 |
| Medium-E,3 | 8 | 48292.01 | 4.63 | 48.50 |
| Medium-E,3 | 9 | 163338.57 | 2.97 | 33.47 |
| total area | | | | 455.88 |
| % impurities | | | | n.a. |
| Clarified Harvest-F,3 | 1 | 7034.19 | 19.07 | 964.89 |
| Clarified Harvest-F,3 | 2 | 8086.00 | 2.68 | 211.65 |
| Clarified Harvest-F,3 | 3 | 9261.06 | 5.53 | 443.49 |
| Clarified Harvest-F,3 | 4 | 9517.88 | 5.42 | 500.84 |
| Clarified Harvest-F,3 | 5 | 11323.50 | 3.53 | 263.60 |
| Clarified Harvest-F,3 | 6 | 12304.80 | 8.34 | 906.01 |
| Clarified Harvest-F,3 | 7 | 13375.63 | 6.11 | 0.00 |
| Clarified Harvest-F,3 | 8 | 13427.27 | 7.77 | 0.00 |
| Clarified Harvest-F,3 | 9 | 13795.45 | 10.06 | 1027.23 |
| Clarified Harvest-F,3 | 10 | 15310.41 | 7.68 | 399.53 |
| Clarified Harvest-F,3 | 11 | 17986.43 | 5.32 | 675.81 |
| Clarified Harvest-F,3 | 12 | 20413.72 | 3.90 | 299.10 |
| Clarified Harvest-F,3 | 13 | 23775.69 | 10.67 | 0.00 |
| Clarified Harvest-F,3 | 14 | 24788.25 | 19.89 | 2012.32 |
| Clarified Harvest-F,3 | 15 | 27198.02 | 6.74 | 418.70 |
| Clarified Harvest-F,3 | 16 | 35747.79 | 5.30 | 146.74 |
| Clarified Harvest-F,3 | 17 | 54198.88 | 6.53 | 219.42 |
| Clarified Harvest-F,3 | 18 | 69483.78 | 9.66 | 565.99 |
| Clarified Harvest-F,3 | 19 | 73883.97 | 10.23 | 323.62 |
| Clarified Harvest-F,3 | 20 | 147799.71 | 36.56 | 681.88 |
| total area | | | | 10060.82 |
| total IgG | | | | 1005.49 |
| % impurities | | | | 90 |
| Flow through-G,3 | 1 | 6338.12 | 4.46 | 743.43 |
| Flow through-G,3 | 2 | 7040.07 | 19.31 | 2083.81 |
| Flow through-G,3 | 3 | 8023.67 | 2.90 | 312.69 |
| Flow through-G,3 | 4 | 8472.55 | 4.40 | 421.66 |
| Flow through-G,3 | 5 | 9545.03 | 16.89 | 3198.23 |
| Flow through-G,3 | 6 | 11324.86 | 7.82 | 1543.17 |
| Flow through-G,3 | 7 | 12312.32 | 43.20 | 3911.14 |
| Flow through-G,3 | 8 | 13392.82 | 7.62 | 0.00 |
| Flow through-G,3 | 9 | 13793.27 | 17.10 | 3671.21 |
| Flow through-G,3 | 10 | 15343.07 | 5.49 | 594.37 |
| Flow through-G,3 | 11 | 18153.19 | 12.54 | 3594.88 |
| Flow through-G,3 | 12 | 20305.64 | 15.09 | 1520.78 |
| Flow through-G,3 | 13 | 24761.17 | 60.32 | 11168.03 |
| Flow through-G,3 | 14 | 27276.83 | 18.87 | 1032.51 |
| Flow through-G,3 | 15 | 36030.90 | 10.44 | 442.12 |
| Flow through-G,3 | 16 | 39493.77 | 8.05 | 400.88 |
| Flow through-G,3 | 17 | 47028.12 | 8.11 | 166.11 |
| Flow through-G,3 | 18 | 49248.06 | 7.08 | 339.56 |
| Flow through-G,3 | 19 | 54179.04 | 10.29 | 355.93 |
| Flow through-G,3 | 20 | 62896.16 | 10.90 | 250.08 |
| Flow through-G,3 | 21 | 69381.29 | 24.74 | 1536.52 |
| total area | | | | 37287.11 |
| % impurities | | | | n.a. |
| Eluate-H,3 | 1 | 13217.32 | 2.09 | 15.18 |
| Eluate-H,3 | 2 | 23769.50 | 3.74 | 138.50 |
| Eluate-H,3 | 3 | 49932.71 | 6.22 | 66.33 |
| Eluate-H,3 | 4 | 74024.36 | 16.19 | 371.10 |
| Eluate-H,3 | 5 | 124274.31 | 6.63 | 137.78 |
| Eluate-H,3 | 6 | 136544.39 | 7.90 | 0.00 |
| Eluate-H,3 | 7 | 147894.25 | 69.36 | 1408.92 |
| total area | | | | 2137.80 |
| total IgG | | | | 1846.34 |
| % impurities | | | | 14 |

TABLE 8

ProteinChip H4

| Spectrum Tag | Peak # | Substance. Mass | Signal/ Noise | MZArea |
|---|---|---|---|---|
| Medium-A,3 | 1 | 5887.435 | 154.8729 | 2307.542 |
| Medium-A,3 | 2 | 6095.129 | 23.0743 | 253.8904 |
| Medium-A,3 | 3 | 9181.094 | 10.98542 | 146.8193 |
| Medium-A,3 | 4 | 12128.92 | 3.009221 | 14.26603 |
| total area | | | | 2722.52 |
| % impurities | | | | n.a. |
| Clarified harvest-B,3 | 1 | 5727.268 | 6.061866 | 95.17794 |
| Clarified harvest-B,3 | 2 | 7075.259 | 12.25289 | 360.7652 |
| Clarified harvest-B,3 | 3 | 11422.08 | 18.32059 | 895.1911 |
| Clarified harvest-B,3 | 4 | 11849.75 | 4.742421 | 329.1265 |
| Clarified harvest-B,3 | 5 | 13941.12 | 45.06168 | 0 |
| Clarified harvest-B,3 | 6 | 14149.16 | 45.56847 | 0 |
| Clarified harvest-B,3 | 7 | 14361.74 | 14.03961 | 0 |
| Clarified harvest-B,3 | 8 | 14581.12 | 6.755022 | 0 |
| Clarified harvest-B,3 | 9 | 17425.9 | 3.943665 | 112.3759 |
| Clarified harvest-B,3 | 10 | 18124.79 | 4.211146 | 209.8651 |
| Clarified harvest-B,3 | 11 | 24162.46 | 5.437719 | 270.5657 |
| Clarified harvest-B,3 | 12 | 25151.49 | 4.977597 | 387.8344 |
| Clarified harvest-B,3 | 13 | 33246.89 | 3.566134 | 139.7081 |
| Clarified harvest-B,3 | 14 | 36614.02 | 3.625673 | 47.26546 |
| total area | | | | 2847.88 |
| % impurities | | | | n.a. |
| Flow through-C,3 | 5 | 11831.68 | 7.041495 | 0 |
| Flow through-C,3 | 6 | 13944.61 | 33.52851 | 0 |
| Flow through-C,3 | 7 | 14157.84 | 38.88574 | 0 |
| Flow through-C,3 | 8 | 14341.51 | 13.18453 | 0 |
| Flow through-C,3 | 9 | 15796.92 | 3.496057 | 548.5688 |
| Flow through-C,3 | 10 | 17424.71 | 3.327024 | 295.0101 |
| Flow through-C,3 | 11 | 18120.25 | 5.451363 | 430.2268 |
| Flow through-C,3 | 12 | 24168.43 | 2.999535 | 230.4684 |
| Flow through-C,3 | 13 | 25206.53 | 5.856752 | 489.9963 |
| Flow through-C,3 | 14 | 33322.85 | 4.759771 | 205.0363 |
| Flow through-C,3 | 15 | 36118.38 | 6.221106 | 243.1876 |
| Flow through-C,3 | 16 | 42547.21 | 9.075226 | 350.7662 |
| Flow through-C,3 | 17 | 50303.98 | 6.133394 | 217.6043 |
| total area | | | | 3010.86 |
| % impurities | | | | n.a. |
| Eluate-D,3 | 1 | 8320.887 | 6.982438 | 31.86119 |
| Eluate-D,3 | 2 | 24177.29 | 5.173549 | 319.6991 |
| Eluate-D,3 | 3 | 50175.22 | 8.781152 | 217.0394 |
| Eluate-D,3 | 4 | 74648.76 | 35.93925 | 1075.105 |
| Eluate-D,3 | 5 | 125014.2 | 18.50343 | 654.359 |
| Eluate-D,3 | 6 | 148581.7 | 212.9426 | 5286.792 |
| total area | | | | 7584.86 |
| total IgG | | | | 6361.90 |
| % impurities | | | | 16 |
| Clarified harvest-F,3 | 1 | 5729.254 | 38.10582 | 889.1119 |
| Clarified harvest-F,3 | 2 | 7090.659 | 17.18724 | 489.537 |
| Clarified harvest-F,3 | 3 | 11436.16 | 135.0857 | 5904.454 |
| Clarified harvest-F,3 | 4 | 11622.48 | 29.62182 | 0 |
| Clarified harvest-F,3 | 5 | 12111.24 | 7.872594 | 0 |
| Clarified harvest-F,3 | 6 | 13936.33 | 44.52504 | 0 |
| Clarified harvest-F,3 | 7 | 14149 | 38.19788 | 0 |
| Clarified harvest-F,3 | 8 | 14366.35 | 11.3847 | 0 |
| Clarified harvest-F,3 | 9 | 14567.59 | 6.337693 | 0 |
| Clarified harvest-F,3 | 10 | 15562.72 | 4.628464 | 401.8075 |
| Clarified harvest-F,3 | 11 | 18098.65 | 3.560782 | 182.0193 |
| Clarified harvest-F,3 | 12 | 24178.96 | 54.74658 | 2359.49 |
| Clarified harvest-F,3 | 13 | 24902.27 | 14.6164 | 0 |
| Clarified harvest-F,3 | 14 | 47973.28 | 24.94115 | 1175.421 |
| Clarified harvest-F,3 | 15 | 71163.87 | 11.5169 | 350.529 |
| Clarified harvest-F,3 | 16 | 148962.2 | 5.608357 | 87.30161 |
| total area | | | | 11839.67 |
| total IgG | | | | 1175.42 |
| % impurities | | | | 90 |
| Flow through-G,3 | 1 | 5716.67 | 12.95565 | 306.0182 |
| Flow through-G,3 | 2 | 6334.993 | 4.461091 | 93.98705 |
| Flow through-G,3 | 3 | 7074.775 | 8.021065 | 179.1698 |
| Flow through-G,3 | 4 | 11430.86 | 62.70494 | 3765.7 |
| Flow through-G,3 | 5 | 11623.5 | 13.72609 | 0 |
| Flow through-G,3 | 6 | 13937.26 | 30.89184 | 0 |
| Flow through-G,3 | 7 | 14139.03 | 25.06366 | 0 |
| Flow through-G,3 | 8 | 14350.55 | 8.848049 | 0 |
| Flow through-G,3 | 9 | 15828.44 | 2.835655 | 199.888 |
| Flow through-G,3 | 10 | 18127.7 | 4.750492 | 675.9793 |
| Flow through-G,3 | 11 | 22353.46 | 4.161511 | 195.3476 |
| Flow through-G,3 | 12 | 24172.3 | 29.60664 | 1450.417 |
| Flow through-G,3 | 13 | 24850.64 | 11.75127 | 0 |
| Flow through-G,3 | 14 | 47875.19 | 17.97307 | 904.1433 |
| Flow through-G,3 | 15 | 71002.91 | 11.96093 | 454.9218 |
| total area | | | | 8225.57 |
| % impurities | | | | n.a. |
| Eluate-H,3 | 1 | 24225.39 | 6.476968 | 272.7851 |
| Eluate-H,3 | 2 | 49850.49 | 7.456789 | 332.1223 |
| Eluate-H,3 | 3 | 74565.84 | 19.31641 | 570.4264 |
| Eluate-H,3 | 4 | 125006.9 | 11.9938 | 244.462 |
| Eluate-H,3 | 5 | 148676.1 | 62.33588 | 1378.798 |
| total area | | | | 2798.59 |
| total IgG | | | | 2281.35 |
| % impurities | | | | 18 |

The invention claimed is:

1. A process for using at least one protein biochip array to monitor contaminant removal during a purification process of a pharmaceutical product produced by a host cell, wherein at least two different samples are taken in the purification process; said monitoring process comprising:

(a) incubating each of the at least two different samples with at least one protein biochip array under binding conditions, (b) detecting the presence of contaminants in each sample bound to the at least one protein biochip array, and (c) comparing results of the detection of bound contaminants to determine whether there was contaminant removal between the at least two different samples.

2. The process of claim 1, wherein a sample is taken before a first purification step of the purification process and after each subsequent purification step.

3. The process of claim 1, wherein a sample obtained after a given purification step is incubated with at least two different protein biochip arrays with different interactive surfaces.

4. The process of claim 1, wherein the contaminants bound to the protein biochip array are detected directly on the array, or are detected indirectly.

5. The process of claim 4, wherein a mass spectrometric approach is used for the direct detection of the contaminants.

6. The process of claim 1, wherein the contaminants detected comprise proteins.

7. The process of claim 6, wherein the contaminants detected comprise host cell proteins.

8. The process of claim 3, wherein a sample obtained after a purification step is incubated with at least three different protein biochip arrays with different interactive surfaces.

9. The process of claim 8, wherein a sample obtained after a purification step is incubated with at least four different protein biochip arrays with different interactive surfaces.

10. The process of claim 3, wherein the pharmaceutical product comprises a protein.

11. The process of claim 10, wherein the protein comprises a fusion protein, an enzyme, a receptor or an antibody.

12. The process of claim 3, wherein the pharmaceutical product comprises a vaccine.

13. In a process for removing contaminants in a purification process of a pharmaceutical product produced by a host cell, wherein the improvement comprises monitoring contaminant removal in accordance with the process of claim 1.

14. The process of claim 13, wherein the sample comprises a host cell culture supernatant.

15. The process of claim 1 or claim 13, wherein the at least one protein biochip array comprises an interactive surface comprising a normal phase interactive surface, an anion exchange interactive surface, a cation exchange interactive surface or a hydrophobic interaction surface.

* * * * *